(12) United States Patent
Zhang et al.

(10) Patent No.: US 7,988,740 B2
(45) Date of Patent: Aug. 2, 2011

(54) KERATIN DYEING COMPOSITIONS COMPRISING A RADICAL SCAVENGER AND USE THEREOF

(75) Inventors: Guiru Zhang, Lebanon, OH (US); Bryan Patrick Murphy, Loveland, OH (US); Jennifer Mary Marsh, Mason, OH (US); Richard Marc Dahlgren, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/763,274

(22) Filed: Apr. 20, 2010

(65) Prior Publication Data
US 2011/0035885 A1 Feb. 17, 2011

Related U.S. Application Data

(60) Provisional application No. 61/170,827, filed on Apr. 20, 2009.

(51) Int. Cl.
*A61Q 5/10* (2006.01)
*C07D 231/00* (2006.01)

(52) U.S. Cl. .............. 8/405; 8/407; 8/408; 8/433; 8/570; 8/573; 548/366.1

(58) Field of Classification Search .............. 8/405, 407, 8/408, 433, 570, 573; 548/36.16
See application file for complete search history.

(56) References Cited

U.S. PATENT DOCUMENTS

| | | | |
|---|---|---|---|
| 3,413,072 A | 11/1968 | Bouboulis | |
| 3,563,684 A | 2/1971 | Charlie | |
| 3,634,013 A * | 1/1972 | Maul et al. | ........................ 8/409 |
| 4,402,700 A | 9/1983 | Feinland | |
| 6,074,438 A | 6/2000 | Lim | |
| 6,210,447 B1 | 4/2001 | Vidal | |
| 6,371,993 B1 | 4/2002 | Moeller | |
| 6,770,102 B1 | 8/2004 | Moeller | |
| 7,056,355 B2 | 6/2006 | Pratt | |
| 2002/0035758 A1 | 3/2002 | Pratt | |
| 2003/0056303 A1 | 3/2003 | Lim | |
| 2004/0107516 A1 | 6/2004 | Pratt | |
| 2005/0091762 A1 | 5/2005 | Lim | |
| 2005/0262647 A1 | 12/2005 | Hoeffkes | |
| 2006/0260072 A1 | 11/2006 | Lim | |
| 2011/0035886 A1 | 2/2011 | Zhang | |

FOREIGN PATENT DOCUMENTS
EP 1413286 B1 4/2004
EP 1759735 B1 12/2007

OTHER PUBLICATIONS

STIC Search Report dated Dec. 8, 2010.*
Diffusion and Distribution of Element-Labelled Surfactants in Human Hair; Int. J. Cos. Sci. 26; pp. 61-69 (2004).
*The World of Hair Colour: A Scientific Companion,* Dr. John Gray, p. 17, 2005.
Kosower, et al.; J. Org. Chem., 1982, 47 (2), pp. 214-221; Publication Date: Jan. 1982.

* cited by examiner

*Primary Examiner* — Eisa B Elhilo
(74) *Attorney, Agent, or Firm* — Laura R. Grunzinger

(57) ABSTRACT

The invention relates to colorant compositions for the oxidative dyeing of keratin fibers comprising radical scavengers in the dyeing composition. The invention also relates to methods for reducing color formation outside of the keratin fiber during oxidative dyeing comprising using such compositions.

17 Claims, No Drawings

US 7,988,740 B2

KERATIN DYEING COMPOSITIONS COMPRISING A RADICAL SCAVENGER AND USE THEREOF

CROSS REFERENCE TO RELATED APPLICATION

This application claims the benefit of U.S. Provisional Application Ser. No. 61/170,827 filed Apr. 20, 2009.

FIELD OF THE INVENTION

The present invention relates to compositions for the oxidative dyeing of keratin fibers comprising radical scavengers. The invention also relates to methods for reducing color formation outside of the keratin fiber during oxidative dyeing comprising using such compositions.

BACKGROUND OF THE INVENTION

The permanent alteration of the color of keratinous fibers, in particular human hair, by the application of hair dyes is well known. In order to provide the consumer with the hair color and the intensity of color desired, a very complex chemical process is utilized. Permanent hair dyeing formulations typically comprise developers (also known as oxidative hair dye precursors or primary intermediates) and couplers (also known as color modifiers or secondary intermediates). Developers are sufficiently small to diffuse into the hair shaft where, once activated by an oxidizing agent, such as hydrogen peroxide, the developers react with other dye compounds, e.g., couplers, to form larger colored complexes, chromophores, in the hair shaft. Couplers, which are also sufficiently small to diffuse into the hair shaft, are generally colorless molecules that form colors in the presence of activated developers. Developers can be used alone or in combination with other developers, and one or more can be used in combination with one or more couplers.

Hair colorant products are typically sold in the form of kits containing a dye component, e.g., a dye lotion, and an oxidizing component, e.g., a hydrogen peroxide solution. The dye component typically has developers (also known as oxidative hair dye precursors or primary intermediates) and couplers (also known as color modifiers or secondary intermediates). In use, the dye component is mixed with the oxidizing component and the resultant mixture is applied to the hair. Developers are sufficiently small to diffuse into the hair shaft where, once activated by an oxidizing agent, such as hydrogen peroxide, the developers react with other dye compounds, e.g., couplers, to form larger colored complexes, chromophores in the hair shaft. Couplers, which are also sufficiently small to diffuse into the hair shaft, are generally colorless molecules that form colors in the presence of activated developers. When the dye component and the oxidizing component are mixed, oxidizing agent present in the oxidizing component begins to oxidize developers present in the dye component and the oxidized developers begin to react with couplers to form chromophores. Thus, some fraction of chromophores is formed outside of the hair fibers, e.g., in the mixing container, before the mixture is applied to the hair. The chromophores formed in the hair shaft do not readily diffuse out of the hair during subsequent washing with water and/or detergents and thereby give the colorant benefit desired by consumers.

When oxidation of the developers takes place outside of the hair, in the mixing container, the dyeing power of the colorant composition (dyeing composition and oxidant composition combined together) gradually decreases and it can become more difficult to achieve a uniform color on the head (between the time when the dyeing composition is applied to the first lock of hair to the time when the dyeing composition is applied to the last lock treated, the dyeing composition is completely oxidized). Inhibiting oxidation of the developers outside of the hair improves dye efficiency, by reducing the premature consumption of dye intermediates. Finally, when oxidation of the developers outside of the hair is inhibited, the color generated by the colorant composition is more reproducible, from user to user. It is therefore desirable that a colorant composition does not form color outside of the hair fiber.

Attempts have been made to inhibit the oxidation of developers outside of the hair and thereby inhibit color formation outside of the hair. For example, 1-phenyl-3-methyl-5-pyrazolone is known to the hair color industry as an antioxidant that can inhibit the oxidation of developers. However, 1-phenyl-3-methyl-5-pyrazolone also penetrates hair and functions as a coupler, forming a pink color upon reaction with p-phenylenediamine (PPD) or its analogs. The use of 1-phenyl-3-methyl-5-pyrazolone as an antioxidant would therefore require reformulation of colorant compositions in order to offset the color change in hair (hair color would shift to a redder hue). Hair colorant products are typically marketed in multiple different shades (sometimes hundreds of different shades), the use of 1-phenyl-3-methyl-5-pyrazolone as an antioxidant may require widespread reformulation, which is undesirable. As such, previous attempts to inhibit the oxidation of developers outside of the hair and inhibit color formation outside of the hair, e.g., using 1-phenyl-3-methyl-5-pyrazolone, have not been successful.

The pyrazol-5-one compounds of the invention inhibit the oxidation of developers outside of the hair and thereby inhibit color formation outside of the hair, without significantly altering the color inside the hair. The use of these compounds, therefore, does not require reformulation of colorant compositions to offset the color shift of the hair as that found when using 1-phenyl-3-methyl-5-pyrazolone.

SUMMARY OF THE INVENTION

This invention relates to a dyeing composition for the oxidative dyeing of keratin fibers comprising at least one coupler compound, at least one developer compound, and at least one radical scavenger selected from pyrazol-5-one compounds, tautomeric compounds thereof, salts thereof, and derivatives thereof, according to the formulas defined herein. This invention further relates to a method for reducing color formation outside of the keratin fiber during oxidative dyeing of the fiber, the method comprising applying such dyeing compositions to the keratin fiber, in the presence of an oxidizing composition, for a period of time sufficient to develop the desired coloration.

DETAILED DESCRIPTION OF THE INVENTION

As used herein the term "hair" to be treated may be "living" i.e. on a living body or may be "non-living" i.e. in a wig, hairpiece or other aggregation of non-living keratinous fibers. Mammalian, particularly human, hair is preferred. However, wool, fur, and other keratin containing fibers are suitable substrates for the compositions according to the present invention.

It is to be understood that within the scope of this invention, numerous potentially and actually tautomeric compounds are involved. Thus, for example, the pyrazol-5-one compounds described herein have keto-enol tautomerism under certain pH conditions and as such general structures shown herein encompass both tautomeric compounds such at the shown below in structures (I) to (III)

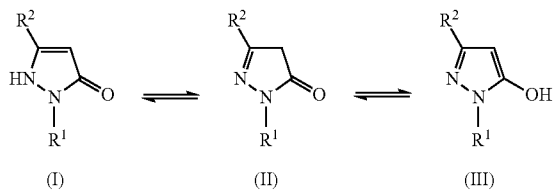

It is to be understood that when this development refers to a particular structure, all of the reasonable additional tautomeric structures are included. In the art, tautomeric structures are frequently represented by one single structure and the invention follows this general practice.

As used herein, "significantly altering the color" of the keratinous fibers or hair means that hair treated with a coloring composition comprising the inhibiting system and measured according the method below has a delta ($\Delta$) E is less than 4 and the absolute value of a delta ($\Delta$) h is less than 5 ($\Delta h<|5|$) compared to the coloring composition without the inhibiting system.

As used herein "reducing color formation outside of the keratin fiber" or "inhibit the composition for the oxidative dyeing of keratin fibers described herein, when in the presence of an oxidizing agent, to form the coloring composition after 30 minutes, when measured according to the method below has a delta ($\Delta$) E of less than 6 at 23° C. compared to the coloring composition without the inhibiting system.

According to the present invention, certain pyrazol-5-one compounds, tautomeric compounds thereof salts thereof, and derivatives thereof, according to the formulas defined herein, inhibit color formation outside of the hair, without significantly altering the color inside the hair. The use of these compounds, therefore, does not require reformulation of colorant compositions to offset the color shift of the hair.

The dyeing compositions of the present invention comprise one or more such radical scavengers as discussed herein and, optionally, one or more chelants.

Radical scavengers, chelants, and other relevant components of the dyeing composition and colorant composition (resulting mixture of dyeing composition and oxidizing composition), are described in detail hereinafter.

Radical Scavenger Compound

The term radical scavenger refers to a species that can react with both hydroxyl radicals and secondary radicals (radicals derived from the oxidation of developers and formulation components, e.g., certain surfactants, adjuvants, solvents, by hydrogen peroxide or hydroxyl radical) to convert the radicals by a series of fast reactions to less reactive species, thereby stopping the free radical chain reaction from propagating further to yield dyes in the dyeing compositing. Radical chemistry is important in the initiation and propagation of color chemistry both in the keratin fiber and in the colorant composition (including developers, couplers, oxidizing agent, solvents, thickeners, surfactants, etc.). Inside the hair and on the surface of the hair, the major radical initiation mechanism is via redox metals, which accelerate dye chemistry by rapidly initiating radical chemistry.

According to the present invention, certain pyrazol-5-one compounds, salts thereof, and derivatives thereof, according to the formulas defined herein, quench radicals to terminate free radical chain reactions, thus inhibiting color formation outside of hair. Furthermore, the pyrazol-5-one compounds of the invention inhibit color formation outside of hair without significantly altering the color inside the hair. The use of these compounds, therefore, does not require reformulation of colorant compositions to offset the color shift of the hair.

Without being bound by theory, it is believed that the pyrazol-5-one compounds of the invention do not the hair to any significant extent under typical oxidative hair-coloring conditions (pH from 8.5-10.5, preferably from 9.0-10.5, room temperature 20-30° C. for 10-45 minutes), thereby not affecting color formation inside the hair. Specifically, it is believed that a non-alkyl substituent at the 3' position of pyrazol-5-one, in contrast to an alkyl substituent at the 3' position, changes the electronic properties of the pyrazolone ring, such that the pyrazolone ring does not couple with primary intermediates, e.g., p-phenylenediamine (PPD), to yield a pink color.

Furthermore, the pyrazol-5-one compounds of the invention are particularly useful for scavenging radicals and inhibiting oxidation at high temperatures. Typically, color forms more rapidly at elevated temperatures. The compounds of the invention inhibit color formation outside the hair at up to about 40° C. Thus, the compounds of the invention provide the benefit of hair-specific color when used in the context of a dryer, heat lamp, or Climazon, e.g., in a salon. The compounds of the invention also provide the benefit of hair-specific color to a user in a hot and/or humid climate. Finally, the pyrazol-5-one compounds of the invention are more efficient than 1-phenyl-3-methyl-5-pyrazolone: at equal concentrations, the pyrazol-5-one compounds of the invention inhibit color formation for a longer period of time than 1-phenyl-3-methyl-5-pyrazolone.

The inventive compositions comprise at least one pyrazol-5-one radical scavenger, tautomeric compounds thereof, salts thereof, or derivatives thereof, according to the following formula:

$R^1$ of formula (I) comprises hydrogen, substituted or unsubstituted alkyl or heteroalkyl, substituted or unsubstituted cycloalkyl or heterocycloalkyl, substituted or unsubstituted alkenyl or heteroalkenyl, substituted or unsubstituted alkynyl or heteroalkynyl, substituted or unsubstituted cycloalkenyl or heterocycloalkenyl, substituted or unsubstituted cycloalkynyl or heterocycloalkynyl, substituted or unsubstituted aryl or heteroaryl, substituted or unsubstituted alkaryl or heteroalkaryl, or substituted or unsubstituted arylkyl or heteroarylkyl. Any substituents that are indicated as being substituted includes a C1-C6 alkyl, linear (as appropriate) or branched, substitution, a hydroxyl substitution, halogen substitution, such as $Cl^-$, $Br^-$; $CO_2^-$, $SO_3^-$, $PO_3^{2-}$, and mixtures thereof.

$R^2$ of formula (I) comprises —$OCH_3$, —$CO_2H$, —C≡$CCO_2H$, —CH═$CHCO_2H$, or —C≡CH.

In certain embodiments, $R^1$ comprises hydrogen, substituted or unsubstituted aryl or heteroaryl, or substituted or unsubstituted alkaryl or heteroalkaryl. In some embodiments, $R^1$ comprises hydrogen or substituted or unsubstituted aryl or heteroaryl. Suitable $R^1$ moieties can be selected from hydrogen, phenyl (unsubstitued aryl), sulfophenyl, disulfophenyl, sulfopropylphenyl, phosphonophenyl, carboxyphenyl, carboxy-sulfophenyl, chloro-sulfophenyl, dichloro-sulfophenyl or n-propylphenyl (substituted aryl), benzyl (unsubstituted alkaryl), pyridinyl or thiazolyl (unsubstituted heteroaryl), carboxylthiophenyl (substituted heteroaryl), cyclohexane (unsubstituted cycloalkyl), sulfoalkyls such as sulfopropy or hydroxylalkyls such as hydroxyethyl (substituted alkyl) and methyl, ethyl and propyl (unsubstituted alkyl).

nyl)pyrazol-5-on-3-yl)propiolic acid, 3-(1H-pyrazol-5-on-3-yl)acrylic acid, 1-(4-carboxyphenyl)-3-ethynylpyrazol-5-one, 3-carboxy-1-(2-chloro-5-sulfophenyl)-pyrazol-5-one, 3-carboxy-1-(2,5-dichloro-4-sulfophenyl)-pyrazol-5-one, 3-carboxy-1-(3,5-disulfophenyl)-pyrazol-5-one, 1-(4-carboxyphenyl)-3-carboxy-1H-pyrazol-5-one, or mixtures thereof.

In certain embodiments, the compositions of the invention comprise 3-carboxy-1H-pyrazol-5-one, 3-carboxy-1-phenyl-pyrazol-5-one, 3-carboxy-1-(4-sulfophenyl)-pyrazol-5-one, 3-carboxy-1-(4-carboxyphenyl)-pyrazol-5-one, or mixtures thereof.

| Compound | R1 | R2 | Full structure |
|---|---|---|---|
| 3-carboxy-1H-pyrazol-5-one | H | —CO2H | |
| 3-carboxy-1-phenylpyrazol-5-one | phenyl | —CO2H | |
| 4-(3-carboxy-1H-pyrazol-5-one-1-yl)benzenesulfonate monosodium salt | 4-sulfophenyl | —CO2H | |
| 1-(4-sulfophenyl)-3-carboxy-1H-pyrazol-5-one | 4-sulfophenyl | —CO2H | |

In some embodiments, $R^2$ comprises —CO$_2$H (carboxyl), —C≡CCO$_2$H (propiloic acid), or —CH═CHCO$_2$H (acrylic acid). In other embodiments, $R^2$ is —CO$_2$H.

In some embodiments, the compositions of the invention comprise 3-carboxy-1H-pyrazol-5-one, 1-(2-sulfophenyl)-3-carboxy-1H-pyrazol-5-one, 4-(3-carboxy-1H-pyrazol-5-one-1-yl)benzenesulfonate monosodium salt, 3-carboxy-1-phenylpyrazol-5-one, 1-(4-sulfophenyl)-3-carboxy-1H-pyrazol-5-one, 1-(3-sulfophenyl)-3-carboxy-1H-pyrazol-5-one, 3-carboxy-1-(pyridine-4-yl)pyrazol-5-one, 3-carboxy-1-(4-phosphonophenyl)-pyrazol-5-one, 1-(3-carboxy-4-sulfophenyl)-3-carboxypyrazol-5-one, 3-carboxy-1-(3-sulfopropyl)-pyrazol-5-one, 3-carboxy-1-(2-hydroxyethyl)pyrazol-5-one, 3-carboxy-1-methylpyrazol-5-one, 3-carboxy-1-cyclohexylpyrazol-5-one, 3-carboxy-1-(4-(3-sulfopropyl)phenyl)-pyrazol-5-one, 3-carboxy-1-(5-carboxythiophen-2-yl)pyrazol-5-one, 1-benzyl-3-carboxypyrazol-5-one, 3-carboxy-1-(4-n-propylphenyl)-pyrazol-5-one, 3-carboxy-1-(thiazol-2-yl)pyrazol-5-one, 3-(1-(4-sulfophe- In some embodiments, the pyrazol-5-one radical scavengers of the invention are polar. Non-polar scavengers typically penetrate hair more readily than polar scavengers, thereby potentially affecting color formation inside the hair.

The pyrazol-5-one radical scavengers of the invention are either commercially available or readily synthesized by known techniques. One method of synthesis is the reaction of diethyl oxalacetate with hydrazine or an appropriate hydrazine derivative.

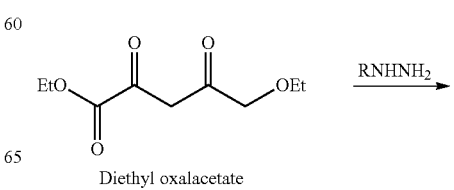

Diethyl oxalacetate

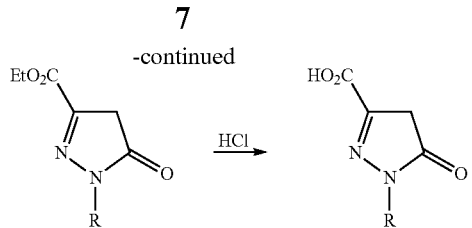

3-carboxy-1H-pyrazol-5-one, for example, can thus be prepared by reacting diethyl oxalacetate with hydrazine to yield 3-(carboethoxy)-pyrazol-5-one, followed by refluxing in aqueous HCl solution to hydrolyze the ethyl ester.

According to the present invention, the colorant compositions (mixture of dyeing composition and oxidizing composition) comprise from about 0.01% to about 10% by weight, in some embodiments, from about 0.05% to about 7% by weight, in certain embodiments, from about 1% to about 5%, in further embodiments, from about 1.5% to about 3% of radical scavenger, salts thereof, derivatives thereof, or mixtures thereof.

Additional Composition Components

The inventive dyeing compositions comprise the radical scavenger compound described above, at least one developer compound, and at least one coupler compound. The dyeing compositions may further comprise additional components, e.g., formulation components, known, conventionally used, or otherwise effective for use in colorant compositions, including but not limited to: solvents; direct dyes; thickeners; chelants; pH modifiers and buffering agents; carbonate ion sources; peroxymonocarbonate ion sources; anionic, cationic, nonionic, amphoteric or zwitterionic surfactants, or mixtures thereof; anionic, cationic, nonionic, amphoteric or zwitterionic polymers, or mixtures thereof; fragrances; buffers; dispersing agents; peroxide stabilizing agents; natural ingredients, e.g. proteins and protein derivatives, and plant extracts; silicones (volatile or non-volatile, modified or non-modified), film-forming agents, ceramides, preserving agents; and opacifiers. Some adjuvants referred to above, but not specifically described below, which are suitable are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose.

Developers

Suitable developers for use in the dyeing compositions described herein include, but are not limited to, p-phenylenediamine derivatives, e.g. benzene-1,4-diamine (commonly known as p-phenylenediamine); 2-chloro-benzene-1,4-diamine; N-phenyl-benzene-1,4-diamine; N-(2-ethoxyethyl)benzene-1,4-diamine; 2-[(4-amino-phenyl)-(2-hydroxyethyl)-amino]-ethanol (commonly known as N,N-bis(2-hydroxyethyl)-p-phenylenediamine); (2,5-diamino-phenyl)-methanol; 1-(2'-Hydroxyethyl)-2,5-diaminobenzene; 2-(2,5-diamino-phenyl)-ethanol; N-(4-aminophenyl)benzene-1,4-diamine; 2,6-dimethyl-benzene-1,4-diamine; 2-isopropyl-benzene-1,4-diamine; 1-[(4-aminophenyl)amino]-propan-2-ol; 2-propyl-benzene-1,4-diamine; 1,3-bis[(4-aminophenyl)(2-hydroxyethyl)amino]propan-2-ol; $N^4,N^4,2$-trimethylbenzene-1,4-diamine; 2-methoxy-benzene-1,4-diamine; 1-(2,5-diaminophenyl)ethane-1,2-diol; 2,3-dimethyl-benzene-1,4-diamine; N-(4-amino-3-hydroxy-phenyl)-acetamide; 2,6-diethylbenzene-1,4-diamine; 2,5-dimethylbenzene-1,4-diamine; 2-thien-2-ylbenzene-1,4-diamine; 2-thien-3-ylbenzene-1,4-diamine; 2-pyridin-3-ylbenzene-1,4-diamine; 1,1'-biphenyl-2,5-diamine; 2-(methoxymethyl)benzene-1,4-diamine; 2-(aminomethyl)benzene-1,4-diamine; 2-(2,5-diaminophenoxy)ethanol; N-[2-(2,5-diaminophenoxy)ethyl]-acetamide; N,N-dimethylbenzene-1,4-diamine; N,N-diethylbenzene-1,4-diamine; N,N-dipropylbenzene-1,4-diamine; 2-[(4-aminophenyl)(ethyl)amino]ethanol; 2-[(4-amino-3-methyl-phenyl)-(2-hydroxy-ethyl)-amino]-ethanol; N-(2-methoxyethyl)-benzene-1,4-diamine; 3-[(4-aminophenyl)amino]propan-1-ol; 3-[(4-aminophenyl)-amino]propane-1,2-diol; N-{4-[(4-aminophenyl)amino]butyl}benzene-1,4-diamine; 2-[2-(2-{2-[(2,5-diaminophenyl)-oxy]ethoxy}ethoxy)ethoxy]benzene-1,4-diamine; 1,3-bis(N(2-Hydroxyethyl)-N-(4-amino-phenyl)amino)-2-propanol; 2,2'-[1,2-Ethanediyl-bis-(oxy-2,1-ethanediyloxy)]-bis-benzene-1,4-diamine; p-aminophenol derivatives such as: 4-amino-phenol (commonly known as p-aminophenol); 4-methylamino-phenol; 4-amino-3-methyl-phenol; 4-amino-2-hydroxymethyl-phenol; 4-amino-2-methyl-phenol; 4-amino-1-hydroxy-2-(2'-hydroxyethylaminomethyl)benzene; 4-amino-2-methoxymethyl-phenol; 5-amino-2-hydroxy-benzoic acid; 1-(5-amino-2-hydroxy-phenyl)-ethane-1,2-diol; 4-amino-2-(2-hydroxyethyl)-phenol; 4-amino-3-(hydroxymethyl)phenol; 4-amino-3-fluoro-phenol; 4-amino-2-(aminomethyl)-phenol; 4-amino-2-fluoro-phenol; 1-hydroxy-2,4-diaminobenzene; o-phenylenediamine derivatives such as: 3,4-Diaminobenzoic acid and salts thereof; o-aminophenol derivatives such as: 2-amino-phenol (commonly known as o-aminophenol); 2,4-diaminophenol; 2-amino-5-methyl-phenol; 2-amino-5-ethyl-phenol; 2-amino-6-methyl-phenol; N-(4-amino-3-hydroxy-phenyl)-acetamide; and 2-amino-4-methyl-phenol; and heterocyclic derivatives such as: pyrimidine-2,4,5,6-tetramine (commonly known as 2,4,5,6-tetraaminopyrimidine); 1-methyl-1H-pyrazole-4,5-diamine; 2-(4,5-diamino-1H-pyrazol-1-yl)ethanol; $N^2,N^2$-dimethyl-pyridine-2,5-diamine; 2-[(3-amino-6-methoxypyridin-2-yl)amino]ethanol; 6-methoxy-$N^2$-methyl-pyridine-2,3-diamine; 2,5,6-triaminopyrimidin-4(1H)-one; pyridine-2,5-diamine; 1-isopropyl-1H-pyrazole-4,5-diamine; 1-(4-methylbenzyl)-1H-pyrazole-4,5-diamine; 1-(benzyl)-1H-pyrazole-4,5-diamine; 1-(4-chlorobenzyl)-1H-pyrazole-4,5-diamine; pyrazolo[1,5-a]pyrimidine-3,7-diamine; 5,6,7-trimethylpyrazolo[1,5-a]pyrimidin-3-ylamine hydrochloride; 7-methylpyrazolo[1,5-a]pyrimidin-3-ylamine hydrochloride; 2,5,6,7-teramethylpyrazolo[1,5-a]pyrimidin-3-ylamine hydrochloride; 5,7-di-tert-butylpyrazolo[1,5-a]pyrimidin-3-ylamine hydrochloride; 5,7-di-trifluoromethyl-pyrazolo[1,5-a]pyrimidin-3-ylamine hydrochloride; 2-methylpyrazolo[1,5-a]pyrimidin-3,7-diamine hydrochloride; 4-hydroxy-2,5,6-triaminopyrimidine; 1-hydroxyethyl-4,5-diaminopyrazole; 2,5-diaminophenylethyl alcohol; and salts thereof.

Additional developers may be selected from N-(3-furylmethyl)benzene-1,4-diamine; N-thiophen-3-ylmethyl-benzene-1,4-diamine; N-(2-furylmethyl)benzene-1,4-diamine: N-thiophen-2-ylmethyl-benzene-1,4-diamine; 3-(2,5-diamino-phenyl)-N-ethyl-acrylamide; 2-[3-(3-amino-phenylamino)-propenyl]-benzene-1,4-diamine; 2-[3-(4-aminophenylamino)-propenyl]-benzene-1,4-diamine; 2-(6-methyl-pyridin-2-yl)-benzene-1,4-diamine; 2-pyridin-2-yl-benzene-1,4-diamine; 2-[3-(4-amino-phenylamino)-propenyl]-benzene-1,4-diamine: 2-[3-(3-amino-phenylamino)-propenyl]-benzene-1,4-diamine; 3-(2,5-diamino-phenyl)-N-ethyl-acrylamide: 2-thiazol-2-yl-benzene-1,4-diamine; 4-hydroxy-benzoic acid (2,5-diamino-benzylidene)-hydrazide; 3'-fluoro-biphenyl-2,5-diamine; 2-propenyl-benzene-1,4-diamine: 2'-chloro-biphenyl-2,5-diamine; N-thiophen-3-ylmethyl-benzene-1,4-diamine; N-(3-furylmethyl)benzene-1,4-diamine; 4'-methoxy-biphenyl-2, 5-diamine; N-(4-amino-benzyl)-benzene-1,4-diamine; 2-methyl-5-[(1-H-pyrrol-2-ylmethyl)-amino]-phenol; 5-[(furan-2-ylmethyl)-amino]-2-methyl-phenol: 5-isopropylamino-2-methyl-phenol; biphenyl-2,4,4'-triamine hydrochloride; 5-(4-amino-phenyl)aminomethyl-benzene-1,3-diamine hydrochloride; 5-phenylaminomethyl-benzene-1,3-diamine hydrochloride; 2-[4-amino-2-(3,5-diamino-benzylamino)-phenoxy]-ethanol hydrochloride; 5-(3-amino-phenyl)aminomethyl-benzene-1,3-diamine hydrochloride; N-(2-amino-benzyl)-benzene-1,3-diamine hydrochloride; N-furan-2-ylmethyl-benzene-1,3-diamine hydrochloride; 2-[(3-amino-phenylamino)-methyl]-phenol hydrochloride; 4-amino-2-propylaminomethyl-phenol; N-benzo[1,3]dioxol-5-ylmethyl-benzene-1,3-diamine hydrochloride; N-[4-amino-2-(2-hydroxy-ethyl)-2H-pyrazol-3-yl]-3-(5-amino-2-hydroxy-phenyl)-acrylamide; 4-amino-2-(isopropylamino-methyl)-phenol; 4-thiophen-3-yl-benzene-1,3-diamine; 5-phenyl aminomethyl-benzene-1,3-diamine hydrochloride; 5-(3-amino-phenyl)aminomethyl-benzene-1,3-diamine hydrochloride; 4-thiophen-3-yl-benzene-1,3-diamine; 2',4'-diamino-biphenyl-4-ol; 5-cyclobutylamino-2-methyl-phenol; 5-cyclobutylamino-2-methyl-phenol; 4-amino-2-(pyridin-3-ylaminomethyl)-phenol; 5-(3-amino-phenyl) aminomethyl-benzene-1,3-diamine hydrochloride; 5-allylaminomethyl-benzene-1,3-diamine hydrochloride; N-(4-amino-benzyl)-benzene-1,3-diamine hydrochloride; N-benzyl-benzene-1,3-diamine hydrochloride; 3-[(3-amino-phenylamino)-methyl]-phenol hydrochloride; N-(4-methoxy-benzyl)-benzene-1,3-diamine hydrochloride; N-thiophen-2-ylmethyl-benzene-1,3-diamine hydrochloride; 4-Amino-2-[(2-hydroxy-5-nitro-phenylamino)-methyl]-phenol; 2',4'-diamino-biphenyl-4-ol hydrochloride; biphenyl-2,4,4'-triamine; 5-(4-amino-phenyl)aminomethyl-benzene-1,3-diamine hydrochloride; 2-[4-amino-2-(3,5-diamino-benzylamino)-phenoxy]-ethanol hydrochloride; 5-allylaminomethyl-benzene-1,3-diamine hydrochloride; 5-(3-amino-phenyl)aminomethyl-benzene-1,3-diamine hydrochloride; N-(4-amino-benzyl)-benzene-1,3-diamine hydrochloride; N-benzyl-benzene-1,3-diamine hydrochloride; 3-[(3-amino-phenylamino)-methyl]-phenol hydrochloride; N-(2-amino-benzyl)-benzene-1,3-diamine hydrochloride; N-(4-methoxy-benzyl)-benzene-1,3-diamine hydrochloride; N-furan-2-ylmethyl-benzene-1,3-diamine hydrochloride; 2-[(3-amino-phenylamino)-methyl]-phenol hydrochloride; N-thiophen-2-ylmethyl-benzene-1,3-diamine hydrochloride; N-benzo[1,3]dioxol-5-ylmethyl-benzene-1,3-diamine hydrochloride; N-[4-amino-2-(2-hydroxy-ethyl)-2H-pyrazol-3-yl]-3-(5-amino-2-hydroxy-phenyl)-acrylamide hydrochloride; 4-amino-2-propylaminomethyl-phenol; 4-amino-2-(isopropylamino-methyl)-phenol hydrochloride; 4-amino-2-[(2-hydroxy-5-nitro-phenylamino)-methyl]-phenol hydrochloride; 2-methyl-5-[(1-H-pyrrol-2-ylmethyl)-amino]-phenol; 5-[(furan-2-ylmethyl)-amino]-2-methyl-phenol; 5-isopropylamino-2-methyl-phenol; 5-cyclobutylamino-2-methyl-phenol; 4-amino-2-(pyridin-3-ylaminomethyl)-phenol; 5-cyclobutylamino-2-methyl-phenol; 4,5-diamino-1-methyl-1H-pyrazole-3-carbonitrile; 3-methoxy-1-propyl-1H-pyrazole-4,5-diamine; 3-methoxy-1-(2-methoxyethyl)-1H-pyrazole-4,5-diamine; 1-(2-aminoethyl)-3-methoxy-1H-pyrazole-4,5-diamine; 8-methoxy-1,2,4,5-tetrahydropyrazolo[5,1-d][1,3,5]oxadiazepin-9-amine; 1-(2-hydroxyethyl)-3-methoxy-1H-pyrazol-4,5-diamine; 1-cyclohexyl-3-methoxy-1H-pyrazole-4,5-diamine; 6-methoxy-1-methyl-2,3-dihydro-1H-imidazo[1,2-b]pyrazol-7-amine; 2-methoxy-4,5,6,7-tetrahydropyrazolo[1,5-a]pyrimidin-3-amine; 3-methoxy-1-octyl-1H-pyrazole-4,5-diamine; 3-methoxy-1-pentyl-1H-pyrazole-4,5-diamine; 6-methoxy-2,3-dihydro-1H-imidazo[1,2-b]pyrazol-7-amine; 3-methoxy-$N^5$,$N^5$-dimethyl-1-propyl-1H-pyrazole-4,5-diamine; 1-hexyl-3-methoxy-1H-pyrazole-4,5-diamine; 1-butyl-3-methoxy-1H-pyrazole-4,5-diamine; 1-isopropyl-3-methoxy-1H-pyrazole-4,5-diamine; 1-ethyl-3-methoxy-1H-pyrazole-4,5-diamine; 3-methoxy-1-(4-methoxybenzyl)-1H-pyrazole-4,5-diamine; 3-methoxy-1-(pyridin-2-yl)-1H-pyrazole-4,5-diamine; 1-(4-ethylphenyl)-3-methoxy-1H-pyrazole-4,5-diamine; 3-methoxy-1-p-tolyl-1H-pyrazole-4,5-diamine; 3-cyano-1-(2-hydroxyethyl)-1H-pyrazole-4,5-diamine; 1-butyl-3-cyano-1H-pyrazole-4,5-diamine; 3-cyano-1-phenyl-1H-pyrazol-4,5-diamine; 3-cyano-1-hexyl-1H-pyrazol-4,5-diamine; 1-butyl-3-cyano-1H-pyrazol-4,5-diamine; 3-cyano-1-(4-methoxybenzyl)-1H-pyrazol-4,5-diamine; 3-cyano-1-isopropyl-1H-pyrazol-4,5-diamine; 1-cyclohexyl-3-fluoro-$N^5$-isopropyl-1H-pyrazole-4,5-diamine; 1-methyl-3-(trifluoromethoxy)-1H-pyrazole-4,5-diamine; 3-fluoro-1-octyl-1H-pyrazole-4,5-diamine; 3-chloro-1-hexyl-1H-pyrazole-4,5-diamine; 3-fluoro-1-(2-hydroxyethyl)-1H-pyrazol-4,5-diamine; 3-chloro-1-(2-hydroxyethyl)-1H-pyrazol-4,5-diamine; 3-chloro-1-(4-hydroxybutyl)-1H-pyrazol-4,5-diamine; 3-chloro-1-(pyridin-2-yl)-1H-pyrazole-4,5-diamine; 3-chloro-1-phenyl-1H-pyrazole-4,5-diamine; 3-chloro-1-ethyl-1H-pyrazole-4,5-diamine; 1-(3-methoxypropyl)-3-(methylsulfinyl)-1H-pyrazole-4,5-diamine; 1-(3-hydroxypropyl)-3-(methylsulfinyl)-1H-pyrazole-4,5-diamine; 1-(4-methoxybenzyl)-3-(methylsulfonyl)-1H-pyrazole-4,5-diamine; 1-methyl-3-(methylsulfonyl)-1H-pyrazole-4,5-diamine; and salts thereof.

In some embodiments, developers include but are not limited to: p-phenylenediamine derivatives such as: 2-methyl-benzene-1,4-diamine; benzene-1,4-diamine; 1-(2,5-diamino-phenyl)-ethanol; 2-(2,5-diamino-phenyl)-ethanol; 2-(methoxymethyl)benzene-1,4-diamine; N-(2-methoxyethyl)benzene-1,4-diamine; 2-[(4-amino-phenyl)-(2-hydroxy-ethyl)-amino]-ethanol; 1-(2,5-diaminophenyl)ethane-1,2-diol; 1-(2'-hydroxyethyl)-2,5-diaminobenzene; 1,3-bis(N-(2-hydroxyethyl)-N-(4-amino-phenyl)amino)-2-propanol; 2,2'-[1,2-ethanediyl-bis-(oxy-2,1-ethanediyloxy)]-bis-benzene-1,4-diamine; N,N-bis(2-hydroxyethyl)-p-phenylenediamine; and mixtures thereof; p-aminophenol derivatives such as: 4-amino-phenol; 4-methylamino-phenol; 4-amino-3-methyl-phenol; 4-amino-2-methoxymethyl-phenol; 1-(5-amino-2-hydroxy-phenyl)-ethane-1,2-diol; 4-amino-2-aminomethylphenol; 4-amino-1-hydroxy-2-(2'-hydroxyethylaminomethyl)benzene; 5-aminosalicylic acid and salts thereof; and mixtures thereof; o-phenylenediamine derivatives such as: 3,4-Diaminobenzoic acid and salts thereof; o-aminophenol derivatives such as: 2-amino-phenol; 2-amino-5-methyl-phenol; 2-amino-6-methyl-phenol; N-(4-amino-3-hydroxy-phenyl)-acetamide; 2-amino-4-methyl-phenol; 2-amino-5-ethyl-phenol; and mixtures thereof; and heterocyclic derivatives such as: pyrimidine-2,4,5,6-tetramine; 1-methyl-1H-pyrazole-4,5-diamine; 2-(4,5-diamino-1H-pyrazol-1-yl)ethanol; 1-(4-methylbenzyl)-1H-pyrazole-4,5-diamine; 1-(benzyl)-1H-pyrazole-4,5-diamine; $N^2$,$N^2$-dimethyl-pyridine-2,5-diamine; 4-Hydroxy-2,5,6-triaminopyrimidine; salts thereof; and mixtures thereof.

In certain embodiments, developers include: 2-methyl-benzene-1,4-diamine; 2-(methoxymethyl)benzene-1,4-diamine; benzene-1,4-diamine; N,N-bis(2-hydroxyethyl)-p-phenylenediamine; 4-amino-phenol; 4-methylamino-phenol; 4-amino-3-methyl-phenol; 2-amino-phenol; 2-amino-5-methyl-phenol; 2-amino-5-ethyl-phenol; 2-amino-6-methyl-phenol; 1-methyl-1H-pyrazole-4,5-diamine; 2-(4,5-diamino- 1H-pyrazol-1-yl)ethanol; 2,5-diaminotoluene; 2,5-diaminophenylethyl alcohol; salts thereof; and mixtures thereof.

Couplers

Suitable couplers for use in the dyeing compositions include, but are not limited to: phenols, resorcinols, naphthols, m-aminophenols, m-phenylenediamines, and heterocyclic compounds, and derivatives thereof such as: 2-amino-5-ethyl-phenol; naphthalene-1,7-diol; benzene-1,3-diol; 4-chlorobenzene-1,3-diol; naphthalen-1-ol; 2-methyl-naphthalen-1-ol; naphthalene-1,5-diol; naphthalene-2,7-diol; benzene-1,4-diol; 2-methyl-benzene-1,3-diol; 7-amino-4-hydroxy-naphthalene-2-sulfonic acid; 2-isopropyl-5-methylphenol; 1,2,3,4-tetrahydro-naphthalene-1,5-diol; 2-chlorobenzene-1,3-diol; 4-hydroxy-naphthalene-1-sulfonic acid; benzene-1,2,3-triol; naphthalene-2,3-diol; 5-dichloro-2-methylbenzene-1,3-diol; 4,6-dichlorobenzene-1,3-diol; 2,3-dihydroxy-[1,4]naphthoquinone; and 1-Acetoxy-2-methyl-naphthalene; m-phenylenediamines such as: 2,4-diaminophenol; benzene-1,3-diamine; 2-(2,4-diamino-phenoxy)-ethanol; 2-[(3-amino-phenyl)-(2-hydroxy-ethyl)-amino]-ethanol; 2-mehyl-benzene-1,3-diamine; 2-[[2-(2,4-diamino-phenoxy)-ethyl]-(2-hydroxy-ethyl)-amino]-ethanol; 4-{3-[(2,4-diaminophenyl)oxy]propoxy}benzene-1,3-diamine; 2-(2,4-diamino-phenyl)-ethanol; 2-(3-amino-4-methoxy-phenylamino)-ethanol; 4-(2-amino-ethoxy)-benzene-1,3-diamine; (2,4-diamino-phenoxy)-acetic acid; 2-[2,4-diamino-5-(2-hydroxy-ethoxy)-phenoxy]-ethanol; 4-ethoxy-6-methyl-benzene-1,3-diamine; 2-(2,4-diamino-5-methyl-phenoxy)-ethanol; 4,6-dimethoxy-benzene-1,3-diamine; 2-[3-(2-hydroxy-ethylamino)-2-methyl-phenylamino]-ethanol; 3-(2,4-diamino-phenoxy)-propan-1-ol; N-[3-(dimethylamino)phenyl]urea; 4-methoxy-6-methyl-benzene-1,3-diamine; 4-fluoro-6-methylbenzene-1,3-diamine; 2-({3-[(2-hydroxyethyl)amino]-4,6-dimethoxyphenyl}-amino)ethanol; 3-(2,4-diaminophenoxy)-propane-1,2-diol; 2-[2-amino-4-(methylamino)-phenoxy]ethanol; 2-[(5-amino-2-ethoxy-phenyl)-(2-hydroxy-ethyl)-amino]-ethanol; 2-[(3-aminophenyl)amino]ethanol; 2,4-Diamino-5-(2'-hydroxyethyloxy)toluene; N,N-Dimethyl-3-ureidoaniline; N-(2-aminoethyl)benzene-1,3-diamine; 4-{[(2,4-diaminophenyl)oxy]methoxy}-benzene-1,3-diamine; 1-methyl-2,6-bis (2-hydroxyethylamino)benzene; and 2,4-dimethoxybenzene-1,3-diamine; m-aminophenols such as: 3-amino-phenol; 2-(3-hydroxy-4-methyl-phenylamino)-acetamide; 2-(3-hydroxy-phenylamino)-acetamide; 5-amino-2-methyl-phenol; 3-amino-2,6-dimethylphenol; 5-(2-hydroxy-ethylamino)-2-methyl-phenol; 5-amino-2,4-dichloro-phenol; 3-amino-2-methyl-phenol; 3-amino-2,6-dimethyl-phenol; 3-amino-2-chloro-6-methyl-phenol; 5-amino-2-(2-hydroxy-ethoxy)-phenol; 2-chloro-5-(2,2,2-trifluoro-ethylamino)-phenol; 5-amino-4-chloro-2-methyl-phenol; 3-cyclopentylamino-phenol; 5-[(2-hydroxyethyl)amino]-4-methoxy-2-methylphenol; 5-amino-4-methoxy-2-methylphenol; 3-(dimethylamino)phenol; 3-(diethylamino)phenol; 5-amino-4-fluoro-2-methylphenol; 5-amino-4-ethoxy-2-methylphenol; 3-amino-2,4-dichloro-phenol; 3-[(2-methoxyethyl)amino]phenol; 3-[(2-hydroxyethyl)amino]phenol; 5-amino-2-ethyl-phenol; 5-amino-2-methoxyphenol; 5-[(3-hydroxy-propyl)amino]-2-methylphenol; 3-[(3-hydroxy-2-methylphenyl)-amino]propane-1,2-diol; 3-[(2-hydroxy-ethyl)amino]-2-methylphenol; 1-methyl-2-hydroxy-4-(2'-hydroxyethyl)amino-benzene; 1,3-bis-(2,4-diaminophenoxy)propane; and heterocyclic derivatives such as: 3,4-dihydro-2H-1,4-benzoxazin-6-ol; 6-methoxyquinolin-8-amine; 4-methylpyridine-2,6-diol; 2,3-dihydro-1,4-benzodioxin-5-ol; 1,3-benzodioxol-5-ol; 2-(1,3-benzodioxol-5-ylamino)ethanol; 3,4-dimethylpyridine-2,6-diol; 5-chloropyridine-2,3-diol; 2,6-dimethoxypyridine-3,5-diamine; 1,3-benzodioxol-5-amine; 2-{[3,5-diamino-6-(2-hydroxy-ethoxy)-pyridin-2-yl]oxy}-ethanol; 1H-indol-4-ol; 5-amino-2,6-dimethoxypyridin-3-ol; 1H-indole-5,6-diol; 1H-indol-7-ol; 1H-indol-5-ol; 1H-indol-6-ol; 6-bromo-1,3-benzodioxol-5-ol; 2-aminopyridin-3-ol; pyridine-2,6-diamine; 3-[(3,5-diaminopyridin-2-yl)oxy]propane-1,2-diol; 5-[(3,5-diaminopyridin-2-yl)oxy]pentane-1,3-diol; indoline-5,6-diol; 3,5-dimethoxypyridine-2,6-diamine; 6-methoxypyridine-2,3-diamine; 3,4-dihydro-2H-1,4-benzoxazin-6-amine; 4-hydroxy-N-methylindole; 1H-5-methylpyrazol-5-one; 1-phenyl-3-methylpyrazol-5-one; 2,6-dimethylpyrazolo [1,5-b]-1,2,4-triazole; 2,6-dimethyl[3,2-c]-1,2,4-triazole; 6-methylpyrazolo-[1,5-a]benzimidazole; 2,6-dihydroxypyridine; 2,6-dihydroxy-3,4-dimethylpyridine; 5-methylpyrazolo[5,1-e]-1,2,3-triazole; 5-methyl-6-chloropyrazolo[5,1-e]-1,2,3-triazole; 5-phenylpyrazolo[5,1-e]-1,2,3-triazole and its addition salts; 1H-2,6-dimethylpyrazolo[1,5-b]-1,2,4-triazole tosylate; 7,8-dicyano-4-methylimidazolo-[3,2-a]imidazole; 2,7-dimethylpyrazolo[1,5-a]pyrimidin-5-one; 2,5-dimethylpyrazolo[1,5-a]pyrimidin-7-one; and 2-methyl-5-methoxymethyl-pyrazolo[1,5-a]pyrimidin-7-one; 6-hydroxybenzomorpholine; and 3-amino-2-methylamino-6-methoxypyridine; salts thereof; and mixtures thereof.

In some embodiments, couplers include but are not limited to: phenol, resorcinol, and naphthol derivatives such as: 2-amino-5-ethyl-phenol; naphthalene-1,7-diol; benzene-1,3-diol; 4-chlorobenzene-1,3-diol; naphthalen-1-ol; 2-methyl-naphthalen-1-ol; naphthalene-1,5-diol; naphthalene-2,7-diol; benzene-1,4-diol; 2-methyl-benzene-1,3-diol; and 2-isopropyl-5-methylphenol; 1,2,4-trihydroxybenzene; 1-acetoxy-2-methylnaphthalene; and mixtures thereof; m-phenylenediamine derivatives such as: benzene-1,3-diamine; 2-(2,4-diamino-phenoxy)-ethanol; 4-{3-[(2,4-diaminophenyl)oxy]propoxy}benzene-1,3-diamine; 2-(3-amino-4-methoxy-phenylamino)-ethanol; 2-[2,4-diamino-5-(2-hydroxy-ethoxy)-phenoxy]-ethanol; and 3-(2,4-diamino-phenoxy)-propan-1-ol; 2,4-diamino-5-(2'-hydroxyethyloxy) toluene; N,N-dimethyl-3-ureidoaniline; 2,4-diamino-5-fluorotoluene; 1-methyl-2,6-bis(2-hydroxyethylamino) benzene; and mixtures thereof; m-aminophenol derivatives such as: 3-aminophenol; 5-amino-2-methyl-phenol; 3-amino-2,6-dimethylphenol; 5-(2-hydroxy-ethylamino)-2-methyl-phenol; and 3-amino-2-methyl-phenol; 1-hydroxy-3-amino-2,4-dichlorobenzene; 1,3-bis-(2,4-diaminophenoxy) propane; 1-hydroxy-2-methyl-5-amino-6-chlorobenzene; 5-Amino-4-chloro-2-methylphenol; and mixtures thereof; and heterocyclic derivatives such as: 3,4-dihydro-2H-1,4-benzoxazin-6-ol; 1,3-benzodioxol-5-ol; 1,3-benzodioxol-5-amine; 1H-indol-4-ol; 1H-indole-5,6-diol; 1H-indol-7-ol; 1H-indol-5-ol; 1H-indol-6-ol; pyridine-2,6-diamine; 2-aminopyridin-3-ol; 4-hydroxy-N-methylindole; 1H-5-methylpyrazol-5-one; 1-phenyl-3-methylpyrazol-5-one; 2,6-dimethylpyrazolo[1,5-b]-1,2,4-triazole; 2,6-dimethyl[3,2-c]-1,2, 4-triazole; 6-methylpyrazolo-[1,5-a]benzimidazole; 2,6-dihydroxypyridine; 2,6-dihydroxy-3,4-dimethylpyridine; 6-hydroxybenzomorpholine; 2,6-dihydroxy-3,4-dimethylpyridine; 3,5-diamino-2,6-dimethoxypyridine; 3-amino-2-methylamino-6-methoxypyridine; salts thereof; and mixtures thereof.

In certain embodiments, couplers include: 2-amino-5-ethyl-phenol; benzene-1,3-diol; 4-chlorobenzene-1,3-diol; 4,6-dichlorobenzene-1,3-diol; 2-methyl-benzene-1,3-diol; 2-amino-4-(2'-hydroxyethyl)aminoanisole; 2,4-diaminobenzyl alcohol; 2,4-diaminophenylethyl alcohol; m-phenylenediamine; 5-amino-2-methyl-phenol; 3-amino-2,6-dimethylphenol; 2,4-diaminophenoxyethanol; 4-amino-2-hydroxyphenoxyethanol; 1-naphthol; 2-methyl-naphthol; 3-aminophenol; 3-amino-2-methylphenol; 4-hydroxy-1,2-methylenedioxybenzene; 4-amino-1,2-methylenedioxybenzene; 4-(2'-hydroxyethyl)amino-1,2-methylenedioxybenzene; 1-Methyl-2-hydroxy-4-(2'-hydroxyethyl) aminobenzene; 2,4-diaminophenetole; 2,4-diamino-5-methylphenetole; 4-hydroxyindole; 3-amino-5-hydroxy-2,6-dimethoxypyridine; and 3,5-diamino-2,6-dimethoxypyridine; benzene-1,3-diamine; 2-aminopyridin-3-ol; 1-phenyl-3-methylpyrazol-5-one; salts thereof; and mixtures thereof.

Additionally, in some embodiments, developers and couplers include 5-methoxymethyl-2-aminophenol; 5-ethyl-2-aminophenol; 5-phenyl-2-aminophenol; 5-cyanoethyl-2-aminophenol; salts thereof; and mixtures thereof.

Any of the developers and couplers described above may be combined to form a mixture of developers and couplers. The dyeing compositions of the present invention will generally comprise from about 0.001% to about 10% by weight of the dyeing composition of developer and coupler dyes. For example, dyeing compositions providing low intensity dyeing such as natural blond to light brown hair shades generally comprise from about 0.001% to about 5%, in some embodiments, from about 0.1% to about 2%, in certain embodiments, from about 0.2% to about 1% by weight of dyeing composition of developers and couplers. Darker shades such as browns and black typically comprise from 0.001% to about 10% by weight, in some embodiments, from about 0.05% to about 7% by weight, in certain embodiments, from about 1% to about 5% by weight of the dyeing composition of developers and couplers. Developer compounds are generally used in approximately equimolar quantities with respect to coupler compounds. The developer compound may, however, be present in a greater or lesser quantity with respect to the coupler compound.

Direct Dyes

The dyeing compositions may also comprise compatible direct dyes, in an amount sufficient to provide coloring, particularly with regard to intensity. Typically, such an amount will range from about 0.05% to about 4%, by weight of the dyeing composition. Suitable direct dyes include but are not limited to: Acid Yellow 1; Acid Orange 3; Disperse Red 17; Basic Brown 17; Acid Black 52; Acid Black 1; Disperse Violet 4; 4-nitro-o-phenylenediamine; 2-nitro-p-phenylenediamine; Picramic Acid; HC Red No. 13; 1,4-bis-(2'-hydroxyethyl)-amino-2-nitrobenzene; HC Yellow No. 5; HC Red No. 7; HC Blue No. 2; HC Yellow No. 4; HC Yellow No. 2; HC Orange No. 1; HC Red No. 1; 2-chloro-5-nitro-N-hydroxyethyl-p-phenylenediamine; HC Red No. 3; 4-amino-3-nitrophenol; 2-hydroxyethylamino-5-nitroanisole; 3-nitro-p-hydroxyethylaminophenol; 2-amino-3-nitrophenol; 6-nitro-o-toluidine; 3-methylamino-4-nitrophenoxyethanol; 2-nitro-5-glycerylmethylaniline; HC Yellow No. 11; HC Violet No. 1; HC Orange No. 2; HC Orange No. 3; HC Yellow No. 9; 4-nitrophenyl aminoethylurea; HC Red No. 10; HC Red No. 11; 2-hydroxyethyl picramic acid; HC Blue No. 12; HC Yellow No. 6; hydroxyethyl-2-nitro-p-toluidine; HC Yellow No. 12; HC Blue No. 10; HC Yellow No. 7; HC Yellow No. 10; HC Blue No. 9; N-ethyl-3-nitro PABA; 4-amino-2-nitrophenyl-amine-2'-carboxylic acid; 2-chloro-6-ethylamino-4-nitrophenol; 6-nitro-2,5-pyridinediamine; HC Violet No. 2; 2-amino-6-chloro-4-nitrophenol; 4-hydroxypropylamino-3-nitrophenol; HC Yellow No. 13; 1,2,3,4-tetrahydro-6-nitrochinoxalin; HC Red No. 14; HC Yellow No. 15; HC Yellow No. 14; 3-amino-6-methylamino-2-nitropyridine; 2,6-diamino-3-((pyridine-3-yl)azo)pyridine; Basic Red No. 118; Basic Orange No. 69; N-(2-nitro-4-aminophenyl)-allylamine; 4-[(4-amino-3-methylphenyl)(4-imino-3-methyl-2,5-cyclohexadien-1-ylidene) methyl]-2-methyl-benzeneamine-hydrochloride; 2-[[4-(dimethyl-amino)phenyl]azo]-1,3-dimethyl-1H-imidazolium chloride; 1-methyl-4-[(methylphenyl-hydrazono)methyl]-pyridinium, methyl sulfate; 2-[(4-aminophenyl)azo]-1,3-dimethyl-1H-imidazolium chloride; Basic Red 22; Basic Red 76; Basic Brown 16; Basic Yellow 57; 7-(2',4'-dimethyl-5'-sulfophenylazo)-5-sulfo-8-hydroxynaphthalene; Acid Orange 7; Acid Red 33; 1-(3'-nitro-5'-sulfo-6'-oxophenylazo)-oxo-naphthalene chromium complex; Acid Yellow 23; Acid Blue 9; Basic Violet 14; Basic Blue 7; Basic Blue 26; sodium salt of mixture of mono- & disulfonic acids (mainly the latter) of quinophthlanone or 2-quinolylindandione; Basic Red 2; Basic Blue 99; Disperse Red 15; Acid Violet 43; Disperse Violet 1; Acid Blue 62; Pigment Blue 15; Acid Black 132; Basic Yellow 29; Disperse Black 9; 1-(N-methylmorpholinium-propylamino)-4-hydroxy-anthraquinone methylsulfate; HC Blue No. 8; HC Red No. 8; HC Green No. 1; HC Red No. 9; 2-hydroxy-1,4-naphthoquinone; Acid Blue 199; Acid Blue 25; Acid Red 4; Henna Red; Indigo; Cochenille; HC Blue No. 14; Disperse Blue 23; Disperse Blue 3; Disperse Blue 377; Basic Red 51; Basic Orange 31; Basic Yellow 87; and mixtures thereof. Preferred direct dyes include but are not limited to: Disperse Black 9; HC Yellow 2; HC Yellow 4; HC Yellow 15; 4-nitro-o-phenylenediamine; 2-amino-6-chloro-4-nitrophenol; HC Red 3; Disperse Violet 1; HC Blue 2; Disperse Blue 3; Disperse Blue 377; Basic Red 51; Basic Orange 31; Basic Yellow 87; and mixtures thereof.

Solvent

The dying composition and colorant composition may comprise a solvent comprising water or a mixture of water and at least one organic solvent to dissolve the compounds present in the dyeing composition or colorant composition that would not typically be sufficiently soluble in water. Suitable organic solvents for use herein include, but are not limited to: $C_1$ to $C_4$ lower alkanols (e.g., ethanol, propanol, isopropanol), aromatic alcohols (e.g. benzyl alcohol and phenoxyethanol); polyols and polyol ethers (e.g., carbitols, 2-butoxyethanol, propylene glycol, propylene glycol monomethyl ether, diethylene glycol monoethyl ether, monomethyl ether, hexylene glycol, glycerol, ethoxy glycol), and propylene carbonate. When present, organic solvents are typically present in an amount ranging from about 1% to about 30%, by weight of the dyeing composition or the colorant composition. In some embodiments, the solvent comprises water, ethanol, propanol, isopropanol, glycerol, 1,2-propylene glycol, hexylene glycol, ethoxy diglycol, or mixtures thereof.

Oxidizing Composition

The oxidizing composition is separate from the dyeing composition, which contains the developers, couplers and inhibiting system. The colorant compositions may comprise an oxidizing composition comprising an oxidizing agent, present in an amount sufficient to bleach melanin pigment in hair and/or oxidize dye precursors (developers).

Typically, such an amount ranges from about 1% to about 20%, in some embodiments, from about 3% to about 15%, in other embodiments, from about 6% to about 12% by weight of the oxidizing composition.

Suitable oxidizing agents include inorganic peroxygen materials capable of yielding hydrogen peroxide in an aqueous medium are suitable and include, but are not limited to: hydrogen peroxide; inorganic alkali metal peroxides (e.g. sodium periodate and sodium peroxide); organic peroxides (e.g. urea peroxide, melamine peroxide); inorganic perhydrate salt bleaching compounds (e.g. alkali metal salts of perborates, percarbonates, perphosphates, persilicates, and persulphates, in some embodiments, sodium salts thereof), which may be incorporated as monohydrates, tetrahydrates, etc.; alkali metal bromates; enzymes; and mixtures thereof. In some embodiments, the oxidizing agent is hydrogen peroxide.

In certain embodiments, the colorant compositions of the invention are air oxidation or auto oxidation hair colorants. In these compositions, dyes are oxidized by atmospheric oxygen.

Thickeners

The dyeing compositions or colorant compositions may comprise a thickener in an amount sufficient to provide the colorant composition with a viscosity so that it can be readily applied to the hair without unduly dripping off the hair and causing mess. Typically, such an amount will be at least about 0.1%, in some embodiments, at least about 0.5%, in other embodiments, at least about 1%, by weight of the colorant composition.

Suitable for use herein are salt tolerant thickeners, including but not limited to: xanthan, guar, hydroxypropyl guar, scleroglucan, methyl cellulose, ethyl cellulose (available as AQUACOTE™), hydroxyethyl cellulose (NATROSOL™), carboxymethyl cellulose, hydroxypropylmethyl cellulose, microcrystalline cellulose, hydroxybutylmethyl cellulose, hydroxypropyl cellulose (available as KLUCEL™), hydroxyethyl ethyl cellulose, cetyl hydroxyethyl cellulose (available as NATROSOL™ Plus 330), N-vinylpyrollidone (available as POVIDONE™), Acrylates/Ceteth-20 Itaconate Copolymer (available as STRUCTURE™ 3001), hydroxypropyl starch phosphate (available as STRUCTURE™ ZEA), polyethoxylated urethanes or polycarbamyl polyglycol ester (e.g. PEG-150/Decyl/SMDI copolymer (available as ACULYN™44), PEG-150/Stearyl/SMDI copolymer (available as ACULYN™ 46), trihydroxystearin (available as THIXCIN™), acrylates copolymer (e.g. available as ACULYN™ 33) or hydrophobically modified acrylate copolymers (e.g. Acrylates/Steareth-20 Methacrylate Copolymer (available as ACULYN™ 22), acrylates/steareth-20 methacrylate crosspolymer (available as ACULYN™ 88), acrylates/vinyl neodecanoate crosspolymer (available as ACULYN™38), acrylates/beheneth-25 methacrylate copolymer (available as ACULYN™ 28), acrylates/C10-30 alkyl acrylate crosspolymer (available as Carbopol® ETD 2020), non-ionic amphophilic polymers comprising at least one fatty chain and at least one hydrophilic unit selected from polyether urethanes comprising at least one fatty chain, and blends of Ceteth—10 phosphate, Di-cetyl phosphate and Cetearyl alcohol (available as CRODAFOS™ CES).

Chelants

Suitable chelants for use herein are carboxylic acids (in particular aminocarboxylic acids) and phosphonic acids (in particular aminophosphonic acids) and polyphosphoric acids (e.g., linear polyphosphoric acids), including the salts and derivatives of these chelants.

Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996).

When related to chelants, the terms "salts and derivatives thereof" mean all salts and derivatives comprising the same functional structure as the chelant they are referring to and that have similar or better chelating properties. These terms include alkali metal, alkaline earth, ammonium, substituted ammonium salts (e.g monoethanolammonium, diethanolammonium, triethanolammonium), esters of chelants having an acidic moiety and mixtures thereof, in particular all sodium, potassium or ammonium salts. The term "derivatives" also includes "chelating surfactant" compounds (these are chelants modified to bear a surfactant moiety while keeping the same chelating functionality). The term "derivatives" also includes large molecules comprising one or more chelating groups having the same functional structure as the parent chelants. An example of these large molecules is polymeric EDDS (ethylenediaminedisuccinic acid).

The colorant compositions (mixture of dyeing composition and oxidizing composition) comprise from about 0.01% to about 5%, in some embodiments, from about 0.25% to about 3%, in certain embodiments, from about 0.5% to about 1% by weight of the colorant composition of chelant, salts thereof, derivatives thereof, or mixtures thereof.

Aminocarboxylic Acid Chelants

Aminocarboxylic acid chelants, as defined herein, are chelants having at least one carboxylic acid moiety (—COOH) and at least one nitrogen atom. Examples of aminocarboxylic acid chelants suitable for use herein include diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N-N'-diglutaric acid (EDDG), 2-hydroxypropylenediamine-N-N'-disuccinic acid (HPDDS), ethylenediaminetetraacetic acid (EDTA), ethylenedicysteic acid (EDC), EDDHA (ethylenediamine-N-N'-bis(ortho-hydroxyphenyl acetic acid)), diaminoalkyldi(sulfosuccinic acids) (DDS), N,N'-bis(2-hydroxybenzyl)ethylenediamine-N,N'-diacetic acid (HBED), salts thereof and derivatives thereof.

Other suitable aminocarboxylic type chelants suitable for use herein are iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, salts thereof and derivatives thereof. Dipicolinic acid and 2-phosphonobutane-1,2,4-tricarboxylic acid are also suitable.

In some embodiments, the aminocarboxylic type chelant is ethylenediamine-N,N'-disuccinic acid (EDDS), derivatives, and salts thereof.

Amino-phosphonic Acid Chelants

The dye compositions and colorant compositions may comprise a chelant selected from amino-phosphonic acid type chelants, salts thereof, derivatives thereof and mixtures thereof. Amino-phosphonic acid type chelants are defined as chelants comprising an amino-phosphonic acid moiety (—$PO_3H_2$) or its derivative —$PO_3R_2$ wherein $R_2$ is a $C_1$ to $C_6$ alkyl or aryl radical.

Suitable amino-phosphonic acid type chelants for use herein are aminotri-(1-ethylphosphonic acid), ethylenediaminetetra-(1-ethylphosphonic acid), aminotri-(1-propylphosphonic acid), and aminotri-(isopropylphosphonic acid). In some embodiments, the amino-phosphonic acid type chelant is aminotri-(methylenephosphonic acid), ethylenediamine-tetra-(methylenephosphonic acid) (EDTMP), diethylene-triamine-penta-(methylenephosphonic acid) (DTPMP), or mixtures thereof.

Other Chelants

Examples of other chelants suitable for use herein include but are not limited to quercetin polyethyleneimines, polyphosphoric acid chelants, etidronic acid, Methylglycine diacetic acid, N-(2-hydroxyethyl)iminodiacetic acid, Iminodisuccinnic acid, N,N-Dicarboxymethyl-L-glutamic acid and N-lauroyl-N,N',N"-ethylenediamine diacetic acid.

In certain embodiments, the dye compositions and colorant compositions comprise diethylenetriamine pentaacetic acid (DTPA), ethylenediamine-N,N'-disuccinic acid (EDDS), ethylenediamine-N,N'-diglutaric acid (EDDG), 2-hydroxypropylenediamine-N,N'-disuccinic acid (HPDDS), glycinamide-N,N'-disuccinic acid (GADS), ethylenediamine-N-N'-bis(ortho-hydroxyphenyl acetic acid) (EDDHA), diethylenetriamine-penta-(methylenephosphonic acid) (DTPMP), salts thereof, derivatives thereof, or mixtures thereof.

In further embodiments, the dye compositions and colorant compositions comprise from about 0.1% to about 5% by weight of colorant composition of diethylene-triamine-penta-(methylenephosphonic acid) and from about 0.1% to about 5% by weight of colorant composition of ethylenediamine-N,N'-disuccinic acid.

pH Modifiers and Buffering Agents

The dyeing compositions may further comprise a pH modifier and/or buffering agent in an amount that is sufficiently effective to adjust the pH of the colorant composition to fall within a range from about 3 to about 13, in some embodiments, from about 8 to about 12, in certain embodiments, from about 9 to about 11.

Suitable pH modifiers and/or buffering agents for use herein include, but are not limited to: ammonia, alkanolamides such as monoethanolamine, diethanolamine, triethanolamine, monopropanolamine, dipropanolamine, tripropanolamine, tripropanolamine, 2-amino-2-methyl-1-propanol, and 2-amino-2-hydroxymethyl-1,3,-propandiol and guanidium salts, alkali metal and ammonium hydroxides and carbonates, in some embodiments, sodium hydroxide and ammonium carbonate, and acidulents such as inorganic and inorganic acids, e.g., phosphoric acid, acetic acid, ascorbic acid, citric acid or tartaric acid, hydrochloric acid, and mixtures thereof.

Carbonate Ion Source

The dyeing compositions may comprise a source of carbonate ions, carbamate ions, or hydrogen carbonate ions, in a sufficient amount to reduce damage to the hair during the coloring process. Typically, such an amount will range from about 0.1% to about 15%, in some embodiments, from about 0.1% to about 10%, in certain embodiments, from about 1% to about 7%, by weight of the colorant composition.

Suitable sources for the ions include but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. In some embodiments, the source of carbonate ions is sodium hydrogen carbonate, potassium hydrogen carbonate, or mixtures thereof. In certain embodiments, the source of carbonate ions is ammonium carbonate, ammonium hydrogen carbonate, or mixtures thereof.

Additional Composition Components

The dyeing compositions may comprise one or more compounds selected from the classes of alkanolamines, amino sugars, amino acids, esters of amino acids and mixtures thereof. Suitable compounds are: 3-amino-1-propanol, 4-amino-1-butanol,5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, or mixtures thereof, or the salts, such as the potassium, sodium, or ammonium salts thereof, or mixtures thereof.

In some embodiments, the dyeing compositions and colorant compositions may comprise glycine, sarcosine, lysine, serine, 2 methoxyethylamine, glucosamine, glutamic acid, morpholine, piperdine, ethylamine, 3 amino-1-propanol, or mixtures thereof. These compounds may be present in the dyeing compositions and colorant compositions at a concentration of from about 0.1% to about 10% by weight, in some embodiments, from about 1% to about 7% by weight of the colorant composition.

Methods of Use

It is understood that the examples of methods of use and embodiments described herein are for illustrative purposes only and that various modifications or changes in light thereof will be suggested to one skilled in the art without departing from the scope of the present invention.

Colorant compositions are usually sold in kits comprising, in individually packaged components such as separate containers, a dyeing composition (also called "dye cream" for emulsions or "dye liquid" for solutions) comprising the oxidative dye precursors and alkalizing agent in a suitable carrier, and; an oxidizing composition comprising a hydrogen peroxide component (also called "hydrogen peroxide cream" for emulsions or "hydrogen peroxide liquid" for solutions). The consumer mixes the dyeing composition and oxidizing composition together immediately before use and applies it onto the hair.

The pyrazol-5-one radical scavengers of the present invention may be comprised within the dye component, e.g., as component parts of a kit. In use, the dye component and the oxidizing component are mixed and the resultant mixture is applied to the hair. Typically, the colorant composition is allowed to act on the hair for about 2 to about 60, in some embodiments, from about 10 to about 45, in certain embodiments, from about 15 to about 30 minutes, at a temperature ranging from about 15° to about 50° C. In some cases, the colorant composition is allowed to act for about 5 to about 10 minutes. In certain cases, the colorant composition is allowed to act for about 2 to about 5 minutes. Thereafter, the hair is rinsed with water, to remove the colorant composition, and then the hair is dried. Optionally, a separate conditioning product may also be applied to the hair after it is rinsed with water but before the hair is dried, generally the conditioning product is also rinsed with water from the hair. The method of coloring the hair is typically a sequential oxidative hair coloring method comprising the steps of at least two sequential oxidative hair color treatments with the colorant composition of the present application wherein the time period between each treatment is from about 1 to about 60 days, in some cases, from about 1 to about 40 days, in certain cases, from about 1 to about 28 days.

The compositions of the present invention may also be applied to hair as part of a pre-treatment to the hair. The pre-treatment composition ("first composition") can be applied immediately before the colorant composition (mixture of oxidizing composition and dyeing composition) is applied or after a longer period of time. In the case of a pre-treatment applied on hair and immediately followed by the application of the colorant composition, in some embodiments, the pre-treatment composition will be left on the hair during the application of the colorant composition, the resulting mixture being rinsed off following the instructed period of time for the color treatment.

Kits

Colorant compositions are usually sold in kits comprising, in individually packaged components, such as separate containers, a dyeing composition (e.g., dye cream for emulsions or dye liquid for solutions), comprising developers, couplers, a buffering/alkalizing agent (typically ammonia), and, optionally, a source of carbonate ion in a suitable carrier, and an oxidizing composition comprising an oxidizing agent (typically hydrogen peroxide, e.g., hydrogen peroxide cream for emulsions or hydrogen peroxide liquid for solutions). The kits further may comprise instructions for usage, gloves and optionally an application instrument such as a dispensing device, brush, comb or the like. A consumer would utilize the instructions for mixing the dyeing composition and oxidizing composition together immediately before use and applies it onto the hair with the application instrument, when present.

The present invention may be utilized in a variety of packaging and dispensing devices.

These dispensing devices can come in the form of separate devices which may be used independently or in combination with one another. Typically, the colorant compositions are contained within separate single or multi compartment containers so that the dyeing composition and the oxidizing composition can be stored separately from one another before use by the end user. The dyeing and oxidizing compositions are then mixed together by a mixing means, such mean including agitating or shaking the resulting mixed composition (colorant composition) within a single closable package or stiffing the resulting mixed composition (colorant composition) within a single package or container and then applied to the end user's hair by an application means.

Methods of Manufacture

The dyeing compositions of this invention may be manufactured using conventional methods. The dyeing compositions may be formed as solutions, preferably as aqueous or aqueous-alcohol solutions. The dyeing compositions may also be formed as thick liquids, creams, gels, or emulsions. Specific examples are provided below.

EXAMPLES

|  | Formulation | | | |
| --- | --- | --- | --- | --- |
| Ingredient | 1 | 2 | 3 | 4 |
| Sodium sulphite | 0.1 | 0.1 | 0.1 | 0.1 |
| Ascorbic Acid | 0.2 | 0.2 | 0.2 | 0.2 |
| Diethylenetriaminepenta(methylenephosphonic acid) | 0.0 | 0.1 | 0.2 | 0.05 |
| Trisodium Ethylenediamine Disuccinate | 1.0 | 0.9 | 0.8 | 0.95 |
| 3-pyrazol-5-one | 1.25 | 1.3 | 1.8 | 3.0 |
| 3-Carboxy-1-phenylpyrazol-5-one | 0.25 | 0.2 | 0.2 | 0.0 |
| Citric Acid | 0.2 | 0.2 | 0.2 | 0.2 |
| Ammonia (30% active) | 4.0 | 4.0 | 4.0 | 4.0 |
| Acrylates Copolymer (ACULYN ® 33A) | 1.0 | 1.0 | 1.0 | 1.0 |
| Oleth 5 | 0.5 | 0.5 | 0.5 | 0.5 |
| Oleth 2 | 1.0 | 1.0 | 1.0 | 1.0 |
| Oleic Acid | 0.9 | 0.9 | 0.9 | 0.9 |
| Cocamidopropyl betaine | 3.0 | 3.0 | 3.0 | 3.0 |
| Etidronic Acid | 0.05 | 0.05 | 0.05 | 0.05 |
| Isopropyl alcohol | 2.5 | 2.5 | 2.5 | 2.5 |
| Hydrogen Peroxide (35% active) | 8.6 | 8.6 | 13 | 13 |
| Soytrimonium Chloride and propylene glycol | 3.0 | 3.0 | 3.0 | 3.0 |
| Simethicone | 0.003 | 0.003 | 0.003 | 0.003 |
| Steareth-21 | 1.0 | 1.0 | 1.0 | 1.0 |
| PEG-50 Hydrogenated Palmamide | 0.5 | 0.5 | 0.5 | 0.5 |
| Oleyl Alcohol | 0.2 | 0.2 | 0.2 | 0.2 |
| Acrylates Steareth-20 Methacrylate Copolymer (ACULYN ® 22) | 0.5 | 0.5 | 1.0 | 1.0 |
| Propylene Glycol | 2.0 | 2.0 | 2.0 | 2.0 |
| Ethoxy Diglycol | 4.2 | 4.2 | 4.2 | 4.2 |
| C11-15 Pareth-9 | 0.5 | 0.5 | 0.5 | 0.5 |
| C12-15 Pareth-3 | 0.8 | 0.8 | 0.8 | 0.8 |
| m-Aminophenol | 0.02 | 0.02 | 0.02 | 0.02 |
| 1-Naphthol | 0.01 | 0.01 | 0.01 | 0.01 |
| N,N-Bis(2-hydroxyethyl)-p-phenylenediamine sulfate | 0.05 | 0.05 | 0.05 | 0.05 |
| Resorcinol | 0.30 | 0.30 | 0.30 | 0.30 |
| p-Phenylenediamine | 0.70 | 0.70 | 0.70 | 0.70 |
| pH adjust to pH 10 | Qs | Qs | Qs | Qs |
| Water | Qs | Qs | Qs | Qs |

|  | Formulation | | | |
| --- | --- | --- | --- | --- |
| Ingredient | 5 | 6 | 7 | 8 |
| Cetearyl alcohol/sodium lauryl sulfate (90/10) | 17.50 | 17.50 | 17.50 | 17.50 |
| Glyceryl stearate SE | 5.50 | 5.50 | 5.50 | 5.50 |
| Glycol distearate | 2.00 | 2.00 | 2.00 | 2.00 |
| Lanolin Alcohol (wool wax, wool grease) | 2.00 | 2.00 | 2.00 | 2.00 |
| Water | 50.00 | 50.00 | 50.00 | 50.00 |
| Hydrogen Peroxide (35% active) | 8.6 | 8.6 | 13 | 13 |
| Sodium Laureth Sulfate/Water (70/30) | 4.00 | 4.00 | 4.00 | 4.00 |
| Sodium Cocoyl Isethionate | 0.46 | 0.46 | 0.46 | 0.46 |
| Sodium Sulfite (Na2SO3) | 0.40 | 0.40 | 0.40 | 0.40 |
| Ascorbic acid | 0.30 | 0.30 | 0.30 | 0.30 |

| | | | | |
|---|---|---|---|---|
| Sodium Sulfate (Na2SO4) | 0.60 | 0.60 | 0.60 | 0.60 |
| Toluene-2,5-diamine sulfate | 0.67 | 0.67 | 0.67 | 0.67 |
| Disodium EDTA | 0.10 | 0.10 | 0.10 | 0.10 |
| Resorcinol | 0.28 | 0.28 | 0.28 | 0.28 |
| 2-Methylresorcinol | 0.04 | 0.04 | 0.04 | 0.04 |
| m-Aminophenol | 0.02 | 0.02 | 0.02 | 0.02 |
| Hydroxyethyl-3,4-methylenedioxyaniline HCl | 0.00 | 0.00 | 0.00 | 0.00 |
| Fragrance | 0.25 | 0.25 | 0.25 | 0.25 |
| Water/Ammonia (75/25) | 6.00 | 6.00 | 6.00 | 6.00 |
| Trisodium Ethylenediamine Disuccinate | 0.9 | 1.0 | 0.8 | 0.95 |
| Diethylenetriaminepenta(methylenephosphonic acid) | 0.10 | 0.00 | 0.20 | 0.05 |
| 3-Carboxy-1H-pyrazol-5-one | 1.00 | 1.50 | 2.00 | 3.00 |
| 3-Carboxy-1-phenylpyrazol-5-one | 0.25 | 0.50 | 0.00 | 0.00 |
| pH adjust to pH 10 | Qs | Qs | Qs | Qs |
| Water | Qs | Qs | Qs | Qs |

| | Formulation | | | |
|---|---|---|---|---|
| Ingredient | 9 | 10 | 11 | 12 |
| Sodium sulphite | 0.1 | 0.1 | 0.1 | 0.1 |
| Ascorbic Acid | 0.1 | 0.1 | 0.1 | 0.1 |
| Ammonium Carbonate | 5.0 | 5.0 | 5.0 | 6.0 |
| Potassium Hydrogen Carbonate | 0.1 | 0.1 | 0.1 | 0.1 |
| Ammonium Acetate | 0.2 | 0.2 | 0.2 | 0.2 |
| Cetearyl Alcohol (and) Dicetyl Phosphate (and) Ceteth-10 Phosphate (CRODAFOS ® CES) | 2.0 | 2.0 | 2.0 | 2.0 |
| Ceteareth-25 (VOLPO ® CS25) | 1.0 | 1.0 | 1.0 | 0.0 |
| Sodium Glycinate | 2.0 | 2.0 | 2.0 | 0.0 |
| Stearyl Alcohol | 2.0 | 2.0 | 2.0 | 0.0 |
| Sodium Hydroxide (50% aqueous solution) | 0.3 | 0.3 | 0.3 | 0.3 |
| Ethylenediaminetetraacetic acid tetrasodium salt | 0.0 | 0.1 | 0.0 | 0.1 |
| Etidronic Acid | 0.5 | 0.5 | 0.5 | 0.5 |
| Hydrogen Peroxide (35% aqueous solution) | 8.6 | 8.6 | 8.6 | 8.6 |
| Amodimethicone (BELSIL ® ADM1100) | 0.0 | 0.0 | 0.0 | 1.0 |
| Acrylates/C10-30 Alkyl Acrylate Crosspolymer | 0.0 | 0.0 | 0.0 | 0.5 |
| Acrylates Steareth-20 Methacrylate Copolymer (ACULYN ® 22) | 0.0 | 0.0 | 0.0 | 1.0 |
| Polyquaternium-22 (MERQUAT ® 295) | 0.2 | 0.2 | 0.2 | 0.0 |
| Polyquaternium-37 & Mineral oil (SALCARE ® SC95) | 0.2 | 0.2 | 0.2 | 0.0 |
| Styrene-PVP Copolymer (POLECTRON ® 430) | 0.1 | 0.1 | 0.1 | 0.5 |
| Xanthan gum | 0.1 | 0.1 | 0.1 | 0.0 |
| Cetyl Alcohol | 2.0 | 2.0 | 2.0 | 0.0 |
| Acrylates copolymer (ACULYN ® 33) | 1.0 | 1.0 | 1.0 | 1.0 |
| p-Phenylenediamine | 0.3 | 0.3 | 0.3 | 0.3 |
| p-Aminophenol | 0.6 | 0.6 | 0.6 | 0.6 |
| N,N-Bis (2-Hydroxyethyl)-p-Phenylenediamine sulfate | 0.2 | 0.2 | 0.2 | 0.2 |
| 2-methyl resorcinol | 0.08 | 0.08 | 0.08 | 0.08 |
| 4-amino-2-hydroxytoluene | 0.5 | 0.5 | 0.5 | 0.5 |
| Resorcinol | 0.3 | 0.3 | 0.3 | 0.3 |
| m-Aminophenol | 0.05 | 0.05 | 0.05 | 0.05 |
| Trisodium Ethylenediamine Disuccinate | 0.9 | 0.8 | 1.0 | 0.7 |
| Diethylenetriaminepenta(methylenephosphonic acid) | 0.1 | 0.2 | 0.0 | 0.3 |
| 3-Carboxy-1H-pyrazol-5-one | 1.0 | 1.0 | 1.5 | 3.0 |
| 3-Carboxy-1-phenylpyrazol-5-one | 0.5 | 1.0 | 0.0 | 0.0 |
| Water | Qs | Qs | Qs | Qs |
| pH adjust to pH 9 | Qs | Qs | Qs | Qs |

Test Data

TABLE 1

The Evaluation Of Color Formation On Hair

| | Hair Color | | | | | | |
|---|---|---|---|---|---|---|---|
| | L* | a* | b* | C* | h | Δh | ΔE |
| Control | 22.81 | 3.05 | 5.12 | 5.96 | 59.22 | | |
| 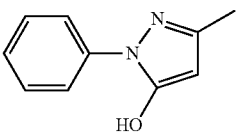<br>1-phenyl-3-methyl-pyrazol-5-one (comparative) | 25.22 | 6.15 | 5.84 | 8.48 | 43.50 | −15.72 | 3.99 |
| Control | 22.81 | 3.05 | 5.12 | 5.96 | 59.22 | | |
| 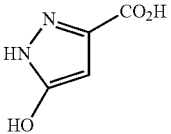<br>3-carboxy-1H-pyrazol-5-one | 26.47 | 3.97 | 6.99 | 8.04 | 60.38 | 1.16 | 4.21 |
| Control | 25.99 | 3.68 | 7.10 | 8.00 | 62.61 | | |
| 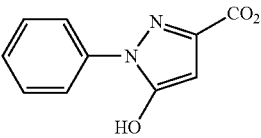<br>3-carboxy-1-phenyl-pyrazol-5-one | 27.30 | 4.23 | 7.55 | 8.65 | 60.72 | −1.89 | 1.49 |

In these experiments a commercial hair colorant was used (NICE 'N EASY® Medium Brown 118) having no chelant (EDDS) present. The indicated radical scavengers in Table 1 were added to this product (2 wt % by weight of the colorant composition) and mixed thoroughly ensuring that the entire amount of added radical scavenger had dissolved. The pH was also checked to ensure it remained above pH 10.

A minimum of 6 g of the resulting mixed product was added to a 1.5 g, 6 inch hair switch of uncolored natural white hair and left for 30 minutes at room temperature (23° C.). After 30 minutes the resulting mixed product was rinsed off the hair for 2 minutes and then dried. The color of the hair was measured with a Minolta 3700d spectrophotometer. For each set of experiments a control (NICE 'N EASY® Medium Brown 118) with no added radical scavenger (control) was included in the test and color of the control hair and the hair treated with the radical scavenger-containing product (resulting mixed product) were compared. The color difference (delta (Δ)E or dE) was calculated as the difference between the final hair color of the control and the final hair color of the radical scavenger-containing product as discussed abovet.

The hue difference (delta (Δ)h or dh) was calculated as the difference in hue between the final hair color of the control and the final hair color of the radical scavenger-containing product. This set of experiments assessed the ability of the radical scavenger to maintain the color formation inside the hair.

Experimental Design—Four Dyeing Mixtures are Prepared as Follows:
(a) Control: 5 g of Nice'n Easy 118 chelant free tint mixed with 5 g of developer (a formula containing 6% $H_2O_2$) from the same package.
(b) Control+hair: 2~2.5 g of Piedmont white virgin hair treated with the dyeing mixture described in (a).
(c) With 2% antioxidant: 0.2 g of the indicated pyrazolone dissolved in 5 g of Nice'n Easy 118 chelant free tint, then mixed with 5 g of developer from the same package, the pH was adjusted back to 10 with 50% aqueous sodium hydroxide.

(d) With 2% antioxidant+hair: 2~2.5 grams of Piedmont white virgin hair treated with the dyeing gel mixture described in (c).

The four different mixtures are contained in separate plastic weighing boats. Pictures are taken under D65 lighting conditions by a DigiEye camera every 5 minutes for 30 minutes. The hair switches are then rinsed, shampooed and dried by a hair blower.

T=45). The color difference (delta ($\Delta$)E or dE) values were calculated according to the equation:

$$dE=[(dL)^2+(da)^2+(db)^2]^{1/2}$$

delta ($\Delta$) a is "da" and delta ($\Delta$)b is "db" where the da and db come from the L*a*b* scale for measuring color. dE and dL

TABLE 2

The Evaluation Of Color Formation In Resulting Mixed Product (Emulsion Or Gel)

| | Gel Color at 5 min | | | | | Gel Color at 35 min | | | | | Gel Color | |
|---|---|---|---|---|---|---|---|---|---|---|---|---|
| | L* | a* | b* | C* | h | L* | A* | b* | C* | h | $\Delta$L** | $\Delta$E** |
| Control | 48.24 | 10.66 | 25.91 | 28.02 | 67.64 | 45.26 | 4.54 | 11.10 | 11.99 | 67.75 | −2.98 | 16.30 |
| 1-phenyl-3-methyl-pyrazol-5-one (comparative) | 73.74 | 19.65 | 40.72 | 45.21 | 64.24 | 81.26 | 21.62 | 40.54 | 45.94 | 61.93 | 7.52 | 7.78 |
| Control | 48.24 | 10.66 | 25.91 | 28.02 | 67.64 | 45.26 | 4.54 | 11.10 | 11.99 | 67.75 | −2.98 | 16.30 |
| 3-carboxy-1H-pyrazol-5-one | 45.61 | 1.96 | 7.05 | 7.32 | 74.46 | 39.72 | 0.93 | 7.04 | 7.10 | 82.47 | −5.89 | 5.98 |
| Control | 48.42 | 11.56 | 26.73 | 29.12 | 66.61 | 39.50 | 6.06 | 13.09 | 14.42 | 65.16 | −8.92 | 17.20 |
| 3-carboxy-1-phenyl-pyrazol-5-one | 64.73 | 12.31 | 19.32 | 22.91 | 57.50 | 57.21 | 15.15 | 21.97 | 26.69 | 55.41 | −7.52 | 8.46 |

The color of the emulsion measured after 30 and 45 minutes using a Nikon D1x camera and the Digi-pix image analysis software. The color of the resulting mixed product at T (time)=30 and 45 minutes was compared to the color of the resulting mixed product at T=5 minutes. The change in color of the resulting mixed product (dE) was calculated from the initial color (T=5 minutes) and final color readings (T=30 and are calculated between different time points ($5^{th}$ vs. $35^{th}$ min.) of the same sample, which are indicative of the scale of color change.

The control sets turn dark much faster than formulations with chelants. The dyeing mass turn dark even before it was put into the light box for the first picture resulting in a $\Delta$L which is relatively small for the control sets.

Negative ΔL (lightness) means the color becomes darker. Positive ΔL means the color becomes lighter. As shown clearly on the table, the chelant free dyeing mass with 3-carboxy pyrazolones darkens similarly or even more than control, which means that they fail to slow down color formation in the resulting mixed product (gel).

delta (Δ) a is "da" and delta (Δ)b is "db" where the da and db come from the L*a*b* scale for measuring color.

These experiments assessed the ability of the indicated radical scavenger to prevent color formation in the resulting mixed product. The lower the reported dE, the better then

TABLE 3

Color Measurement Of Dye Forming In Resulting Mixed Product Without Hair At Room Temperature (23° C.)

| Radical Scavenger | Color at T = 30 mins | | | Color at T = 45 mins | | | dE versus T = 5 mins | |
|---|---|---|---|---|---|---|---|---|
| | L | C | h | L | c | h | 30 mins | 45 mins |
| 1-phenyl-3-methyl-pyrazol-5-one (comparative) | 70.3 | 40.2 | 67.5 | 21.8 | 10.1 | 346.9 | 8.0 | 63.3 |
| 3-carboxy-1H-pyrazol-5-one | 73.5 | 45.4 | 71.6 | 73.7 | 47.1 | 72.1 | 1.9 | 3.4 |
| 3-carboxy-1-phenyl-pyrazol-5-one | 55.2 | 55.0 | 67.5 | 54.2 | 54.9 | 68.0 | 4.4 | 5.2 |

In these experiments a commercial hair colorant was used (NICE 'N EASY® Medium Brown 118) which comprises EDDS chelant. The indicated radical scavengers in Tables 3-5 were added to this product (2 wt % by weight of the colorant composition) and mixed thoroughly ensuring that the entire amount of added radical scavenger had dissolved. The pH was also checked to ensure it remained above pH 10. Two sets of experiments were performed. The first set of experiments was with the final mixed emulsion with no hair added. 10 g of the resulting mixed product (emulsion or gel) was placed in a weigh boat at room temperature (23° C.) and is shown above in Table 1. The second set was run at 40° C. and is shown in Table 2.

The color of the emulsion measured after 30 and 45 minutes using a Nikon D1x camera and the Digi-pix image analysis software. The color of the resulting mixed product at T (time)=30 and 45 minutes was compared to the color of the resulting mixed product at T=5 minutes. The change in color of the resulting mixed product (dE) was calculated from the initial color (T=5 minutes) and final color readings (T=30 and T=45). The color difference (delta (Δ)E or dE) values were calculated according to the equation:

$$dE = [(dL)^2 + (da)^2 + (db)^2]^{1/2}$$

performance of the radical scavenger to prevent color formation in the resulting mixed product.

TABLE 4

Color Measurement Of Dye Forming In Resulting Mixed Product Without Hair At 40° c.

| Radical Scavenger | Color at T = 30 mins | | | Color at T = 45 mins | | | dE vers T = 5 mins | |
|---|---|---|---|---|---|---|---|---|
| | L | C | h | L | c | h | 30 mins | 45 mins |
| 1-phenyl-3-methyl-pyrazol-5-one (comparative) | 20.9 | 4.3 | 2.4 | 19.1 | 2.2 | 30.3 | 59.1 | 60.7 |
| 3-carboxy-1H-pyrazol-5-one | 68.0 | 39.5 | 79.0 | 66.0 | 39.2 | 78.6 | 10.4 | 11.8 |

A similar process for collecting the information was follows as that in Table 2 and 3. These experiments assessed the ability of the indicated radical scavenger to prevent color formation in the resulting mixed product. The lower the reported dE, the better then performance of the radical scavenger to prevent color formation in the resulting mixed product.

TABLE 5

Color Measurement Of Dye Forming In Hair

| Radical Scavenger | Color of Hair after 35 mins | | | Change in hair color vs Control (no scavenger) | |
|---|---|---|---|---|---|
| | L | C | h | dh | dE |
| 1-phenyl-3-methyl-pyrazol-5-one (comparative) | 32.6 | 10.8 | 52.5 | 14.8 | 3.6 |
| 3-carboxy-1-phenyl-pyrazol-5-one | 30.6 | 11.3 | 67.8 | 0.0 | 0.2 |
| 3-carboxy-1H-pyrazol-5-one | 28.4 | 7.4 | 59.4 | 0.3 | 3.6 |

Table 5 shows a set of results of the resulting mixed product (NICE 'N EASY® Medium Brown 118 with 2 wt % of radical scavenger) with added hair. A minimum of 6 g of the resulting mixed product was added to a 1.5 g, 6 inch hair switch of uncolored natural white hair and left for 30 minutes at room temperature (23° C.). After 30 minutes the resulting mixed product was rinsed off the hair for 2 minutes and then dried. The color of the hair was measured with a Minolta 3700d spectrophotometer. For each set of experiments a control (NICE 'N EASY® Medium Brown 118) with no added radical scavenger (control) was included in the test and color of the control hair and the hair treated with the radical scavenger-containing product (resulting mixed product) were compared. The color difference (delta (Δ)E or dE) was calculated as the difference between the final hair color of the control and the final hair color of the radical scavenger-containing product as discussed abovet.

The hue difference (delta (Δ)h or dh) was calculated as the difference in hue between the final hair color of the control and the final hair color of the radical scavenger-containing product. This set of experiments assessed the ability of the radical scavenger to maintain the color formation inside the hair.

The results show that the 3-carboxy-substituted pyrazolone structures give significantly less color in the emulsion than the 3-methyl-substituted pyrazolone and maintain the color in the hair (i.e. little change in dE of the emulsion versus T=5 minutes and little change in dE and dh of the hair versus the control with no radical scavenger).

L=measure of lightness and has a value between 0 and 100.
C=measure of chroma (saturation).
h=measure of hue and is represented as an angle ranging from 0° to 360° (angles 0°-90° are reds, oranges and yellows; angles 90°-180° are yellows, yellow-greens and greens; 180°-270° are greens, blue-greens and blues; 270-360 are blues, purples and magentas, and return to red) (*The World of Hair Colour: A Scientific Companion*, Dr. John Gray, page 17, 2005).

TABLE 6

The Evaluation Of Color Formation On Hair With Indicated Pyrazolones And Diethylenetriamine Pentaacetic Acid (DTPA) Chelant

| | Hair Color | | | | | | |
|---|---|---|---|---|---|---|---|
| | L* | a* | b* | C* | h | Δh | ΔE |
| Control | 25.74 | 3.95 | 7.21 | 8.22 | 61.31 | | |
| 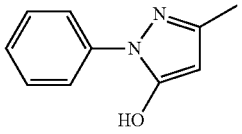<br>1-phenyl-3-methyl-pyrazol-5-one (comparative) | 26.38 | 6.25 | 6.21 | 8.81 | 44.83 | −16.48 | 2.59 |
| Control | 31.91 | 4.52 | 7.47 | 8.73 | 58.83 | | |
| 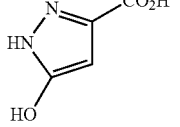<br>3-carboxy-1H-pyrazol-5-one | 30.44 | 4.66 | 7.51 | 8.84 | 58.17 | −0.66 | 1.48 |
| Control | 24.46 | 3.94 | 6.18 | 7.33 | 57.51 | | |
| 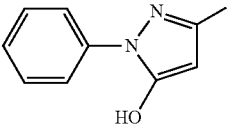<br>3-carboxy-1-phenyl-pyrazol-5-one | 26.65 | 3.95 | 6.28 | 7.42 | 57.82 | 0.31 | 2.19 |

Experimental Design—Four Dyeing Mixtures are Prepared as Follows:
(e) Control: 5 g of L'Oreal PREFERENCE® 5, medium brown tint, which contains DTPA chelant) is mixed with 5 g of developer (a formula containing 6% $H_2O_2$) from the same package.
(f) Control+hair: 2~2.5 g of Piedmont white virgin hair treated with the dyeing mixture described in (a).
(g) With 2% antioxidant: 0.2 g of pyrazolone was dissolved in 5 g of Preference 5 tint, then mixed with 5 g of developer from the same package, the pH was adjusted back to 10 with 50% aqueous sodium hydroxide.
(h) With 2% antioxidant+hair: 2~2.5 grams of Piedmont white virgin hair treated with the dyeing gel mixture described in (c).

The four different mixtures are contained in separate plastic weighing boats. Pictures are taken under D65 lighting conditions by a DigiEye camera every 5 minutes for 30 minutes as discussed above in Table 2 and 3. The hair switches are then rinsed, shampooed and dried with a hair blower.

Experimental conditions are identical as the ones listed in Table 5 with the data collection the same as that in Table 3. dE and dL are calculated between different time points ($5^{th}$ vs. $35^{th}$ min.) of the same sample, which are indicative of the scale of color change.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. When more than one composition are used during a treatment, as in mixing of the components of a typical oxidative dye product, the total weight to be considered is the total weight of all the compositions applied on the hair simultaneously (i.e. the weight found "on head") unless otherwise specified. The term "weight percent" may be denoted as "wt. %" herein.

The dimensions and values disclosed herein are not to be understood as being strictly limited to the exact numerical

TABLE 6

The evaluation of color formation With Indicated Pyrazolones And Diethylenetriamine Pentaacetic Acid (DTPA) Chelant gel without hair

| | Gel Color at 5 min | | | | | Gel Color at 35 min | | | | | Gel Color | |
|---|---|---|---|---|---|---|---|---|---|---|---|---|
| | L* | a* | b* | C* | h | L* | A* | b* | C* | h | ΔL** | ΔE** |
| Control | 55.55 | 19.81 | 33.89 | 39.26 | 59.69 | 50.23 | 8.40 | 14.83 | 17.04 | 60.47 | −5.32 | 22.84 |
| 1-phenyl-3-methyl-pyrazol-5-one (comparative) | 65.95 | 23.77 | 48.31 | 53.84 | 63.80 | 72.03 | 19.65 | 46.57 | 50.55 | 67.12 | 6.08 | 7.55 |
| Control | 54.22 | 22.24 | 34.90 | 41.38 | 57.49 | 44.14 | 8.71 | 13.17 | 15.79 | 56.52 | −10.08 | 27.51 |
| 3-carboxy-1H-pyrazol-5-one | 63.43 | 19.75 | 38.87 | 43.60 | 63.06 | 57.34 | 19.59 | 41.65 | 46.03 | 64.81 | −6.09 | 6.70 |
| Control | 57.48 | 15.90 | 30.23 | 34.16 | 62.25 | 54.96 | 7.97 | 16.60 | 18.41 | 64.35 | −2.52 | 15.97 |
| 3-carboxy-1-phenyl-pyrazol-5-one | 71.68 | 14.96 | 20.11 | 25.06 | 53.35 | 79.06 | 16.11 | 23.76 | 28.71 | 55.86 | 7.38 | 8.31 | values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition for the oxidative dyeing of keratin fibers comprising:
   a. at least one radical scavenger selected from pyrazolone compounds according to formula (I):

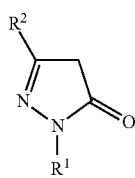

(I)

wherein $R^1$ comprises hydrogen, substituted or unsubstituted alkyl or heteroalkyl, substituted or unsubstituted cycloalkyl or heterocycloalkyl, substituted or unsubstituted alkenyl or heteroalkenyl, substituted or unsubstituted alkynyl or heteroalkynyl, substituted or unsubstituted cycloalkenyl or heterocycloalkenyl, substituted or unsubstituted cycloalkynyl or heterocycloalkynyl, substituted or unsubstituted aryl or heteroaryl, substituted or unsubstituted alkaryl or heteroalkaryl, or substituted or unsubstituted arylkyl or heteroarylkyl; and
   wherein $R^2$ comprises —$OCH_3$, —$CO_2H$, —C≡$CCO_2H$, —CH═$CHCO_2H$, or —C≡CH;
   b. at least one coupler compound; and
   c. at least one developer compound.

2. The composition of claim 1, wherein $R^2$ is —$CO_2H$.

3. The composition of claim 2, wherein $R^1$ comprises hydrogen or substituted or unsubstituted aryl or heteroaryl.

4. The composition of claim 1, wherein said radical scavenger comprises 3-carboxy-1H-pyrazol-5-one, 1-(2-sulfophenyl)-3-carboxy-1H-pyrazol-5-one, 4-(3-carboxy-1H-pyrazol-5-one-1-yl) benzenesulfonate monosodium salt, 3-carboxy-1-phenylpyrazol-5-one, 1-(4-sulfophenyl)-3-carboxy-1H-pyrazol-5-one, 1-(3-sulfophenyl)-3-carboxy-1H-pyrazol-5-one, 3-carboxy-1-(pyridine-4-yl)pyrazol-5-one, 3-carboxy-1-(4-phosphonophenyl)-pyrazol-5-one, 1-(3-carboxy-4-sulfophenyl)-3-carboxypyrazol-5-one, 3-carboxy-1-(3-sulfopropyl)-pyrazol-5-one, 3-carboxy-1-(2-hydroxyethyl)pyrazol-5-one, 3-carboxy-1-methylpyrazol-5-one, 3-carboxy-1-cyclohexylpyrazol-5-one, 3-carboxy-1-(4-(3-sulfopropyl)phenyl)-pyrazol-5-one, 3-carboxy-1-(5-carboxythiophen-2-yl)pyrazol-5-one, 1-benzyl-3-carboxypyrazol-5-one, 3-carboxy-1-(4-n-propylphenyl)-pyrazol-5-one, 3-carboxy-1-(thiazol-2-yl)pyrazol-5-one, 3-(1-(4-sulfophenyl)pyrazol-5-on-3-yl)propiolic acid, 3-(1H-pyrazol-5-on-3-yl)acrylic acid, 1-(4-carboxyphenyl)-3-ethynylpyrazol-5-one, 3-carboxy-1-(2-chloro-5-sulfophenyl)-pyrazol-5-one, 3-carboxy-1-(2,5-dichloro-4-sulfophenyl)-pyrazol-5-one, 3-carboxy-1-(3,5-disulfophenyl)-pyrazol-5-one, 1-(4-carboxyphenyl)-3-carboxy-1H-pyrazol-5-one, or mixtures thereof.

5. A composition according to claim 1, wherein said composition further comprises a chelant.

6. A composition according to claim 5 wherein said chelant comprises a carboxylic acid chelant, a phosphonic acid chelant, a polyphosphoric acid chelant, salts thereof, derivatives thereof, or mixtures thereof.

7. A composition according to claim 6 wherein said chelant comprises diethylenetriamine pentaacetic acid (DTPA), ethylenediamine-N,N'-disuccinic acid (EDDS), ethylenediamine-N,N'-diglutaric acid (EDDG), 2-hydroxypropylenediamine-N,N'-disuccinic acid (HPDDS), glycinamide-N,N'-disuccinic acid (GADS), ethylenediamine-N-N'-bis(ortho-hydroxyphenyl acetic acid) (EDDHA), diethylene-triamine-penta-(methylenephosphonic acid) (DTPMP), salts thereof, derivatives thereof, or mixtures thereof.

8. A composition according to claim 7 wherein said composition comprises diethylene-triamine-penta-(methylenephosphonic acid) and ethylenediamine-N,N'-disuccinic acid.

9. A composition according to claim 5 wherein said composition comprises from about 0.25% to about 3.0% of said chelant.

10. A composition according to claim 9 wherein said composition comprises from about 0.5% to about 1.0% of said chelant.

11. A composition according to claim 1, wherein said developer compound comprises methoxymethyl-p-phenylenediamine, 2,6-dichloro-4-aminophenol, 5-amino-2-ethyl-phenol, 2,5-toluenediamine sulphate, N-phenyl-p-phenylenediamine, p-phenylenediamine, p-methylaminophenol, N,N-bis(2-hydroxyethyl)-p-phenylenediamine, 3-methyl-p-aminophenol, hydroxyethyl-p-phenylenediamine, hydroxypropyl-bis-(N-hydroxyethyl)-p-phenylenediamine, 1-hydroxyethyl-4.5-diaminopyrazole, 2,2'-methylenebis-4-aminophenol, 5-methyl-o-aminophenol, 5-ethyl-o-aminophenol, or mixtures thereof.

12. A composition according to claim 1 wherein said coupler compound comprises a phenol, a resorcinol, a naphthol, a m-aminophenol, a m-phenylenediamine, a heterocyclic compound, or mixtures thereof.

13. A composition according to claim 12 wherein said coupler compound comprises 2-amino-5-ethyl-phenol; naphthalene-1,7-diol; benzene-1,3-diol; 4-chlorobenzene-1,3-diol; naphthalen-1-ol; 2-methyl-naphthalen-1-ol; naphthalene-1,5-diol; naphthalene-2,7-diol; 2-methyl-benzene-1,3-diol; 1-acetoxy-2-methylnaphthalene; benzene-1,3-diamine; 2-(2,4-diamino-phenoxy)-ethanol; 4-{3-[(2,4-diaminophenyl)oxy]propoxy}benzene-1,3-diamine; 2-[2,4-diamino-5-(2-hydroxy-ethoxy)-phenoxy]-ethanol; 3-(2,4-diamino-phenoxy)-prop an-1-ol; 2,4-diamino-5-(2'-hydroxyethyloxy) toluene; 1-methyl-2,6-bis(2-hydroxyethylamino)benzene; 3-amino-phenol; 5-amino-2-methyl-phenol; 3-amino-2,6-dimethylphenol; 3-amino-2-methyl-phenol; 1-methyl-2-hydroxy-4-(2'-hydroxyethyl)aminobenzene; 1-hydroxy-3- amino-2,4-dichlorobenzene; 1,3-Bis-(2,4-diaminophenoxy) propane; 1-hydroxy-2-methyl-5-amino-6-chlorobenzene; 5-amino-4-chloro-2-methylphenol; 3,4-dihydro-2H-1,4-benzoxazin-6-ol; 1,3-benzodioxol-5-ol; 1,3-benzodioxol-5-amine; 1H-indol-4-ol; 1H-indole-5,6-diol; 1H-indol-7-ol; 1H-indol-5-ol; 1H-indol-6-ol; pyridine-2,6-diamine; 2-aminopyridin-3-ol; 4-hydroxy-N-methylindole; 2,6-dihydroxypyridine; 2,6-dihydroxy-3,4-dimethylpyridine; 6-hydroxybenzomorpholine; 2,6-dihydroxy-3,4-dimethylpyridine; 3,5-diamino-2,6-dimethoxypyridine; 3-Amino-2-methylamino-6-methoxypyridine; or mixtures thereof.

14. A composition according to claim 1, wherein said composition further comprises an oxidizing agent, a source of carbonate ion, an alkalizing agent, or a mixture thereof.

15. A method of treating hair comprising the steps of contacting the hair with a composition according to claim 1 and subsequently rinsing said composition from the hair.

16. The method of claim 15, wherein said composition is applied as a pre-treatment.

17. A hair colouring kit comprising:
   a. an individually packaged first component comprising an oxidizing agent and
   b. an individually packaged second component comprising:
      i. at least one radical scavenger selected from pyrazolone compounds according to formula (I):

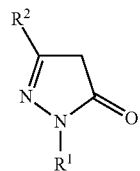

(I)

wherein $R^1$ comprises hydrogen, substituted or unsubstituted alkyl or heteroalkyl, substituted or unsubstituted cycloalkyl or heterocycloalkyl, substituted or unsubstituted alkenyl or heteroalkenyl, substituted or unsubstituted alkynyl or heteroalkynyl, substituted or unsubstituted cycloalkenyl or heterocycloalkenyl, substituted or unsubstituted cycloalkynyl or heterocycloalkynyl, substituted or unsubstituted aryl or heteroaryl, substituted or unsubstituted alkaryl or heteroalkaryl, or substituted or unsubstituted arylkyl or heteroarylkyl; and wherein $R^2$ comprises —$OCH_3$, —$CO_2H$, —C≡$CCO_2H$, —CH=$CHCO_2H$, or —C≡CH;

ii. at least one developer compound; and
iii. at least one coupler compound.

* * * * *